United States Patent [19]

Dyrek

[11] Patent Number: 5,409,500
[45] Date of Patent: Apr. 25, 1995

[54] VERSATILE THERAPEUTIC COLD PACK

[75] Inventor: Dan Dyrek, North Quincy, Mass.

[73] Assignee: Ergomed, Inc., Mashpee, Mass.

[21] Appl. No.: 153,882

[22] Filed: Nov. 17, 1993

Related U.S. Application Data

[63] Continuation of Ser. No. 901,760, Jun. 22, 1992, abandoned.

[51] Int. Cl.$^6$ .............................................. A61F 7/00
[52] U.S. Cl. ..................................... 607/111; 607/112; 607/114
[58] Field of Search .................. 607/96, 104, 108–112, 607/114

[56] References Cited

U.S. PATENT DOCUMENTS

| | | | |
|---|---|---|---|
| 2,071,706 | 2/1937 | Reach | 607/109 X |
| 3,463,161 | 8/1969 | Andrassy | 607/110 |
| 4,765,338 | 8/1988 | Turner et al. | 607/110 |
| 5,133,348 | 7/1992 | Mayn | 607/108 |
| 5,163,425 | 11/1992 | Nambu et al. | 607/110 |
| 5,230,335 | 7/1993 | Johnson, Jr. et al. | 607/104 |

*Primary Examiner*—Angela D. Sykes
*Attorney, Agent, or Firm*—Morse, Altman, Dacey & Benson

[57] ABSTRACT

A therapeutic cold pack is provided for temporary affixation to an area of the human body. The cold pack comprises a pair of hermetic barrier layers that are heat sealed together throughout a plurality of articulations defining a plurality of compartments. A refrigerant gel, such as ethylene glycol, is contained within the compartments and has a high specific heat such that after becoming cooled it absorbs a large quantity of heat while undergoing phase change on heating. The plurality of compartments is distributed throughout an extended area. Adjoining compartments are hinged to each other along intersecting axes. The compartments are adapted to be folded with respect to each other along the axes into a configuration that is snugly seated against an irregular three dimensional anatomical surface. A relatively large velcro-type micro-fastener area is located at the back of the cold pack. Elastomeric straps characterized having restricted micro-fastener areas cooperate with the large micro-fastener area for versatile connection on the anatomical surface. The structure is sufficiently versatile to accommodate anatomical surfaces of substantially different sizes, shapes and locations.

3 Claims, 19 Drawing Sheets

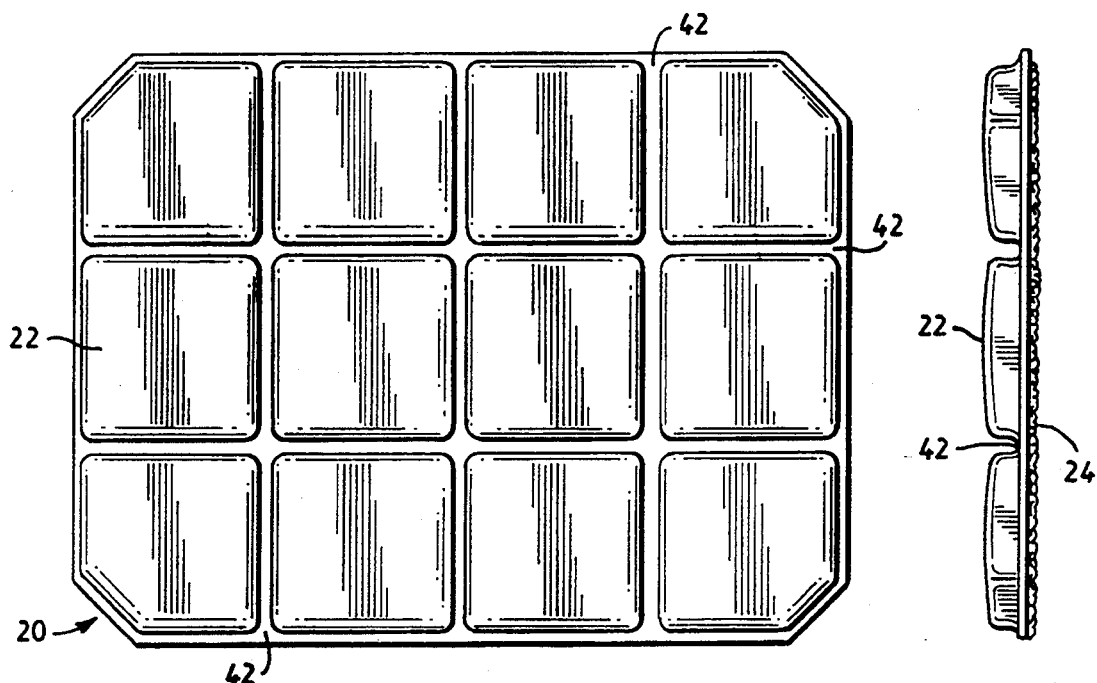
FIG. 1
FIG. 3
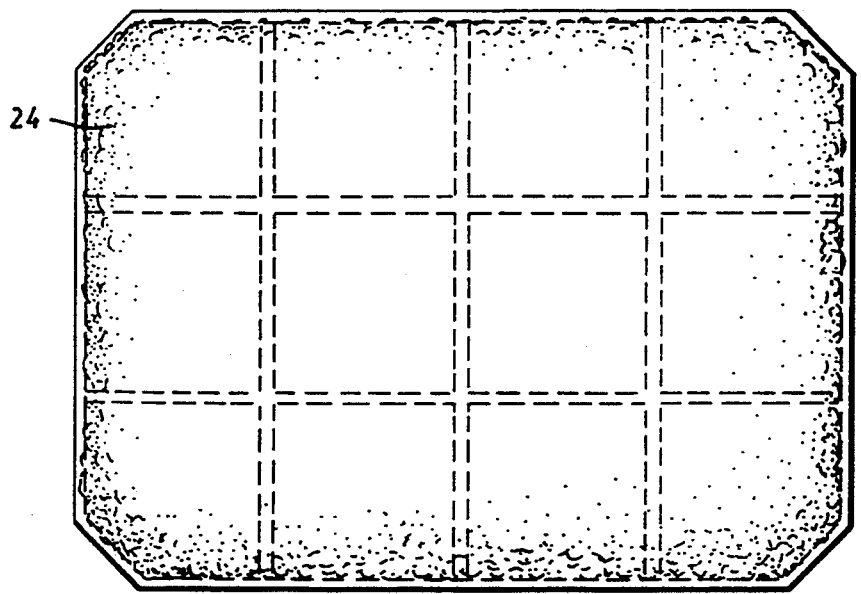
FIG. 2
FIG. 4

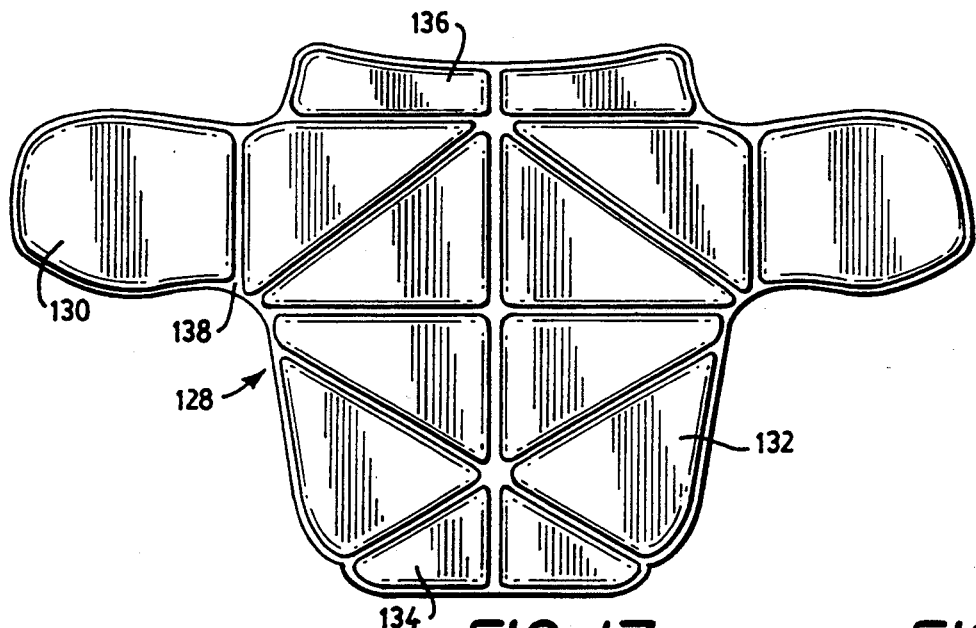
FIG. 17   FIG. 20
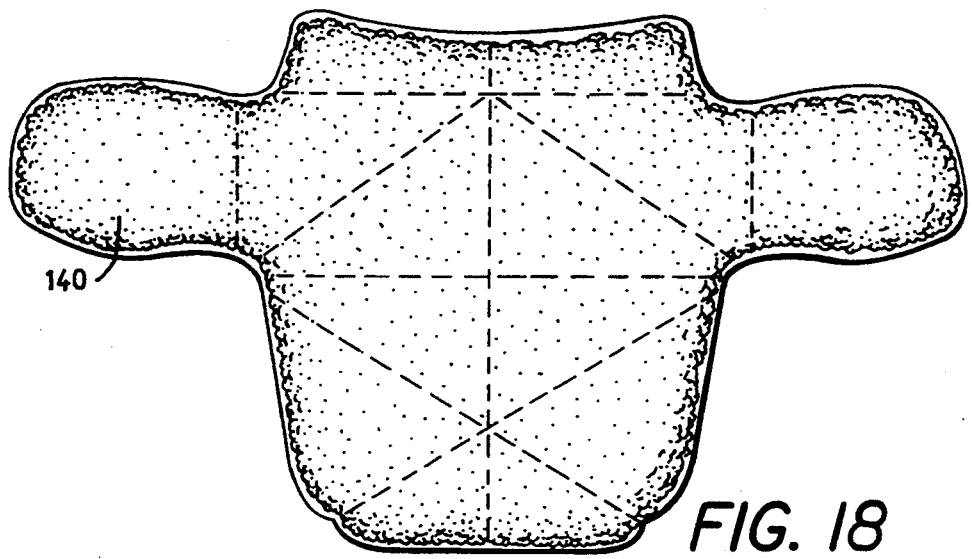
FIG. 18
FIG. 19

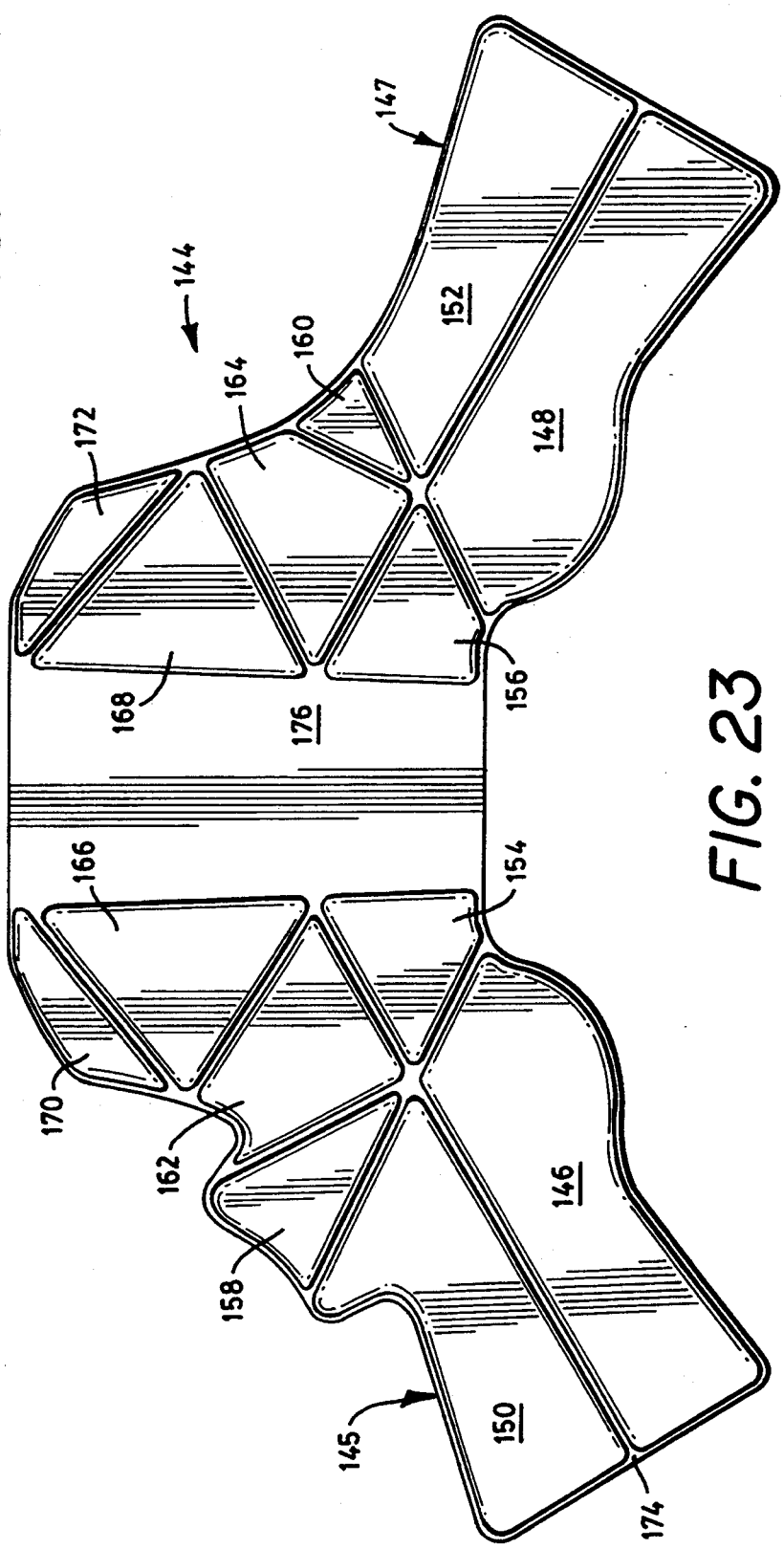

VERSATILE THERAPEUTIC COLD PACK

This is a continuation of application Ser. No. 07/901,760 filed on Jun. 22, 1992, now abandoned.

1. Field of the Invention

The present invention relates to cryotherapy, i.e. cooling as a therapeutic medical procedure, and, more particularly, to cryotherapeutic bandages, compresses or like local anatomical overlays having compartments that contain a cold gel for causing local cooling of various parts of the human body.

2. The Prior Art

There have been a variety of proposals for local anatomical cooling. It is well known that tissue temperature may be reduced by convection (flowing air over a local area of skin), by evaporation (spraying a local area of skin with a highly volatile liquid), or by conduction (application of a solid, liquid or gaseous medium having a temperature lower than that of skin tissue). Such cooling reduces pain by decreasing electrical conduction velocity in nerves, reduces inflammation by decreasing cellular permeability, and limits topical swelling by causing capillary constriction. Conductive cooling has been found to be advantageous in many applications because it is thought to be more readily controllable than other cooling techniques.

A conductive cooling source may be therapeutically helpful if secured in contact with a specified anatomical region under an assured pressure for a specified duration. A conductive cooling source may be therapeutically ineffective or even harmful if contact with the designated anatomical region and predetermined pressure are not assured. Furthermore, it is economically necessary that such a cooling source be affixed in position readily and predictably, often by semi-skilled personnel, in accordance with medical instructions, and removed easily for cleansing and re-use.

A variety of so-called cold packs have been proposed. This type of product often is in the form of a bandage, compress or other local overlay having a plurality of cooling gel compartments, a distribution of predeterminedly anchored straps, and a plurality of mating fasteners on the body of the overlay and at free ends of the straps. The purpose of this arrangement is to meet a variety of physical and anatomical conditions, although in practice only a limited number of these conditions have been concurrently achieved in the past. In some devices of this type, the mating fasteners take the form of patches with VELCRO-type micro-loop and micro-hook mating surfaces. Often such cold packs are not sufficiently conformable throughout for snug, comfortable and reliable contact with and for effective distributed negative thermal conduction from the cooling gel to the intended anatomical region.

A BRIEF DESCRIPTION OF THE INVENTION

A primary object of the present invention is to provide a novel conduction cooling, local anatomical overlay comprising an array of cooling gel compartments defined between a pair of hermetic barrier layers of a particular compliant, slightly elastomeric, polymeric composition throughout an extended area, at least a retaining layer having a VELCRO-type fastener surface throughout a major portion of the extended area, and a plurality of elastomeric straps having at their free ends patches with VELCRO-type micro-fastener surfaces of restricted area. The compartments of the array are separated, or articulated, by intersecting rectilinear seals so that flexing of the array along the seals can occur along complex three dimensional configurations. Preferably, the composition of the gel remains a fluid slurry within the operative cooling temperature of approximately the freezing point of water. The solid geometry of the maximum volume of any compartment and the volume of its gel content are substantially equal so that the gel cannot be squeezed within any compartment substantially into a corner or end. Technically, major deformation of the cold pack occurs at the rectilinear articulations and minor deformation occurs within any compartment by virtue of some elastomeric give in the barrier layers.

The arrangement is such that the overlay, after the gel has been cooled but remains fluid, may be articulately and resiliently conformed to an anatomical surface to establish a desired overall configuration, and may be secured in that configuration under desired pressure by extending the straps under greater or lesser tension between points at which the fastener surface of the retaining layer and the fastener surfaces of the end patches are mated. It is preferred in some cases that the fastener surface of the retaining layer be composed of micro-loops and the fastener surfaces of the strap patches be composed of micro-hooks. The reason for this arrangement is that the relatively smooth feel of the exposed micro-loop surface is considerably more pleasant than would be the relatively scratchy feel of the micro-hook surface.

Another object of the present invention is to provide a series of such cold packs, which are specifically designed for application to such anatomical locales as: the lumbar back region; the wrist; the knee or elbow; the cervical back region, i.e. the neck and upper back; the foot; the face; the leg; and the pelvis. In these embodiments, related functional regions include associated cooling gel compartments of rectangular and non-rectangular profile, and related spacer regions which act together to conform the assemblage to a specific anatomical locale, with the cooling gel compartments in active thermally conductive contact therewith.

Other objects of the present invention will in part be obvious and will in part appear hereinafter.

For a fuller understanding of the nature and objects of the present invention, reference is made to the following specification, which is to be taken in connection with the accompanying drawing, wherein:

BRIEF DESCRIPTION OF THE DRAWINGS

FIG. 1 is a top view of a cold pack for general use embodying the present invention;

FIG. 2 is a bottom view of the cold pack of FIG. 1;

FIG. 3 is a side edge view of the cold pack of FIG. 1;

FIG. 4 is a front edge view of the cold pack of FIG. 1;

FIG. 17 is a top plan view of another cold pack for use in the cervical locale in accordance with the present invention;

FIG. 18 is a bottom plan view of the cold pack of FIG. 18;

FIG. 19 is a front edge view of the cold pack of FIG. 18;

FIG. 20 is a side edge view of the cold pack of FIG. 18;

FIG. 23 is a top plan view of another cold pack for use on the front in accordance with the present invention;

FIG. 25 is a front edge view of the cold pack of FIG. 23;

DETAILED DESCRIPTION OF THE PREFERRED EMBODIMENTS

The Cold Pack of FIGS. 1-7

Figure 5:
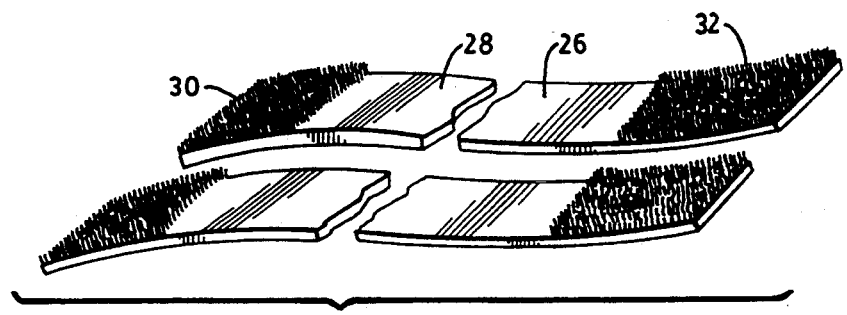
FIG. 5 is a perspective view of a series of straps in accordance with the present invention.

The product of FIGS. 1 to 7 is shown as a conductive cooling source in the form of a cold pack 20. As shown (FIG. 1), cold pack 20 comprises a plurality of cooling gel compartments 22 distributed between and defined by a pair of barrier layers or sheets to be described in more detail below. It will be observed that compartments 22 are distributed substantially throughout the extended area of the product. At the rear of the product (FIG. 2), also distributed throughout this extended area, is a VELCRO-type fastener layer 24. Also constituting necessary components of the illustrated product are a plurality of straps 26 (FIG. 5), each of which includes an elastomeric band 28 and a pair of patches 30, 32, which are affixed at the free ends of the strap. Preferably, extended fastener layer 24 has an outer surface that provides a VELCRO-type micro-loop texture. Preferably, each of restricted patches 30, 32 has an outer surface that provides a VELCRO-type micro-hook texture.

Figure 6:
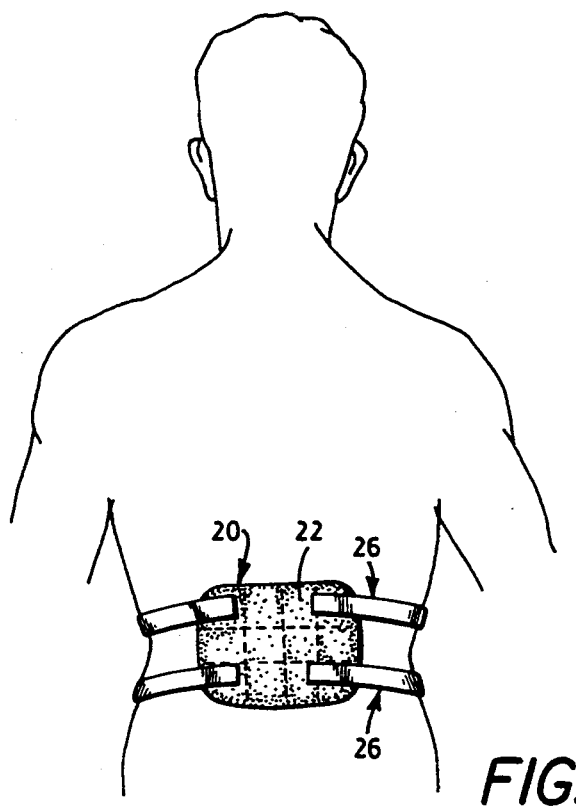
FIG. 6 is a view of the cold pack of FIG. 1 in use at the lumbar region of the back.
Figure 7:
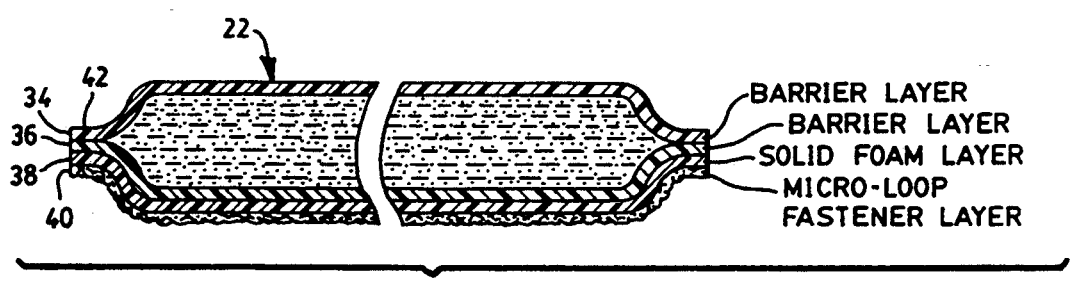
FIG. 7 is an exaggerated cross-sectional view, partly broken away, of a compartment of the cold pack of FIG. 1.
Figure 8:
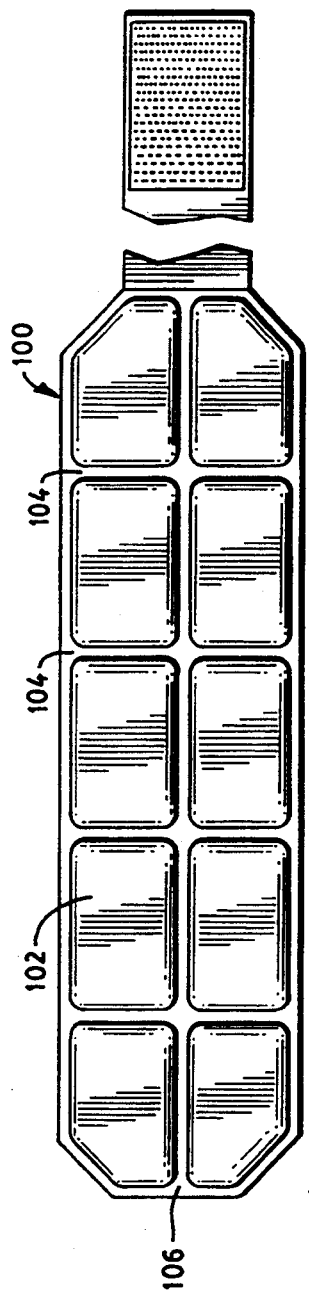
FIG. 8 is a top plan view of an alternative cold pack for general use in accordance with the present invention.
Figure 9:
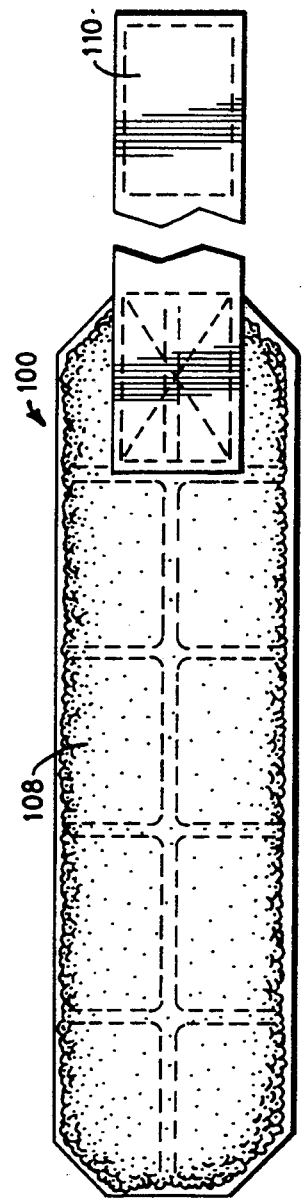
FIG. 9 is a bottom plan view of the cold pack of FIG. 8.
Figure 10:
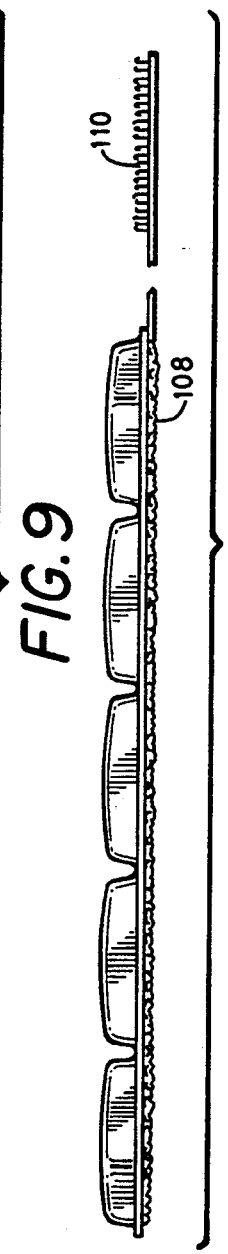
FIG. 10 is a front edge view of the cold pack of FIG. 8.
Figure 11:
FIG. 11 is a side edge view of the cold pack of FIG. 8.

Details of the construction of the product of FIGS. 1 to 6 are shown in FIG. 7. Each of gel compartments 22 is defined by a pair of superimposed fluid barrier layers 34, 36 and contains a refrigerant composition that may be repeatedly cooled to a slush and thawed. Superposed on one of the barrier layers is an inner solid foam insulating layer 38 and an outer VELCRO-type micro-fastener layer 40. All of layers 34, 36, 38 and 40 are coextensive, composed of a thermoplastic, and heat sealed to provide hermetically sealed, intersecting rectilinear articulations 42 separating the compartments. Barrier layers 34 and 36 are slightly elastomeric so that the storage volume of the compartment can be substantially maintained when it is filled by the fluid gel, but can be deformed slightly when contacting a complex surface under pressure. This arrangement precludes any major constriction of the compartment and the squeezing of most of the gel into only a corner or extremity of the compartment.

Exemplary materials of which the product of FIGS. 1 to 7 is composed are as follows. Barrier layers 34, 36 preferably are composed of solid polyurethane that ranges from 0.003 to 0.010 inch thick, and, more preferably in some applications approximately 0.008 inch thick. Solid foam layer 38 preferably is composed of a polyurethane foam that ranges from 0.01 to 0.10 inch thick, and, more preferably in some applications is approximately 0.09 inch thick. Fastener layer 40 has a thermoplastic inner stratum and a micro-loop fastener outer stratum. In order to ensure excellent bonding at articulations 42, all of the aforementioned layers must be composed of thermoplastic compositions that are chemically compatible. Polyurethane is preferred in all cases because it tends to retain its flexibility even at the low temperature of the gel when below 0° Celsius.

As is well known, polyurethane is the reaction product of (1) unsaturated polyesters or polyethers, and (2) isocyanates. Preferred polyurethanes are those sold under the trade designations MP-1880 and MP-1882S by JPS Elastomerics Corporation, Northampton, Mass., and have the characteristics indicated in the following tables.

TABLE I

| MP-1880 & MP-1882S POLYETHER POLYURETHANES GENERAL PROPERTIES | | |
|---|---|---|
| | MP-1880 | MP-1882S |
| | | (15 mil sheet) |
| Tensile Properties: D638 | | |
| Modulus @ 100% strain psi | 1000 | 800 |
| Modulus @ 300% strain psi | 1500 | 1100 |
| Modulus @ break psi | 7000 | 6000 |
| Modulus of elasticity up to 10% strain psi | 30 | 25 |
| Elongation @ break % | 450 | 550 |
| Set @ break % | 40 | 40 |
| Set @ 100% strain % | | |
| Tear Properties: | | |
| Die C D624 pli | 400 | 375 |
| Split D1938 pli | 350 | 300 |
| Abrasion Resistance, mg. | 30 | 100 |

TABLE I-continued

MP-1880 & MP-1882S POLYETHER POLYURETHANES GENERAL PROPERTIES

|  | MP-1880 | MP-1882S (15 mil sheet) |
|---|---|---|
| weight loss per 1000 cycles, 1000 gm. load, H18 C501 mg. | | |
| Maximum Service Temperatures, continuous °F. | −60 to 200 | −60 to 175 |
| Set, Method A, 22 hr. 70° C. D395 % | 15 | 25 |
| Set, Method B, 22 hr. 70° C. D395 % | 25 | 30 |
| Durometer D2240 | 85A | 82A |
| Thermal Properties: Melting point range °F. | 350 to 390 | 290 to 330 |
| Specific Gravity D792 | 1.14 | 1.14 |

TABLE II

MP-1880 & MP-1890 POLYETHYLERS GENERAL PROPERTIES

|  | MP-1880 | MP-1890 |
|---|---|---|
| Tensile Properties: (D638) | | |
| Modulus @ 100% strain psi | 1000 | 1500 |
| Modulus @ 300% strain psi | 2000 | 3000 |
| Modulus @ break psi | 7000 | 8000 |
| Modulus of elasticity up to 10% strain psi | 35 | 50 |
| Elongation @ break % | 450 | 400 |
| Set @ break % | 35 | 25 |
| Set @ 100% strain % | 5 | 5 |
| Tear Properties | | |
| Die C (D624) pli | 400 | 500 |
| Split (D1938) pli | 375 | 450 |
| Abrasion Resistance, Mg. Weight loss/1000 cycles gm load, H18 (ASTMC501) mg | 30 | 25 |
| Maximum Service Temperatures, continuous, °F. | −60 to 200 | −60 to 225 |
| Compression Properties (shape factor = 0.56) | | |
| Set Method A 22 hrs 70° C. (D395) % | 12 | 12 |
| Set Method B 22 hrs 70° C. (D395) % | 23 | 30 |
| Durometer (D2240) | 85A | 90A |

TABLE III

MP 1880 & MP1890 POLYETHERS GENERAL PROPERTIES

|  | MP1880 | MP1890 |
|---|---|---|
| Thermal Properties Melting Point Range, °F. | 350 to 390 | 380 to 420 |
| Specific Gravity (D792) | 1.14 | 1.14 |
| Yield Factors Square feet/pound/ml. thickness | 168.8 | 168.8 |
| Vapor Transmission Rates (E96) (inverted @ 22 ± 2° C. grams weight loss/100 sq. in./24 hr @ 20 mil thickness) | | |
| Distilled water | 2.1 | 1.2 |
| Superunleaded gasoline | 20 | 10 |
| Humid aging resistance (90% relative humidity at 160° F. 70° C.) | Excellent | Excellent |

TABLE IV

MP-1495 & MP-1890 POLYESTERS GENERAL PROPERTIES

|  | MP1495 | MP2080 |
|---|---|---|
| Tensile Properties: | | |
| Modulus @ 100% strain psi | 1400 | 800 |
| Modulus @ 300% strain psi | 3500 | 1800 |
| Modulus @ break psi | 7000 | 7000 |
| Modulus of elasticity | 60 | 30 |

TABLE IV-continued

MP-1495 & MP-1890 POLYESTERS GENERAL PROPERTIES

|  | MP1495 | MP2080 |
|---|---|---|
| up to 10% strain psi | | |
| Elongation @ break % | 400 | 400 |
| Set @ break % | 20 | 30 |
| Set @ 100% strain % | 6 | 3 |
| Tear Properties | | |
| Die C (D624) pli | 550 | 425 |
| Split (D1938) pli | 670 | 400 |
| Abrasion Resistance, big. weight loss/100 cycles 1000 gm load, H18 (ASTMC501) mg | 100 | 70 |
| Maximum Service Temperatures, Continuous, °F. | −40 to 200 | −40 to 225 |
| Compression Properties (shape factor = 0.56) | | |
| Set Method A 22 hrs 70° C. (D395) % | 20 | 11 |
| Set Method B 22 hrs 70° C. (D395) % | 25 | 18 |
| Durometer (D2240) | 95A | 85A |

TABLE V

MP-1495 & MP-2080 POLYESTERS GENERAL PROPERTIES

|  | MP1495 | MP2080 |
|---|---|---|
| Thermal Properties Melting Point Range, °F. | 340 to 380 | 360 to 400 |
| Specific Gravity (D792) | 1.21 | 1.20 |
| Yield Factors Square feet/pound/ml. thickness | 159.0 | 160.3 |
| Vapor Transmission Rates (E96) (Inverted @ 22 ± 2° C. grams weight loss/100 sq. in./24 hr @ 20 mil thickness) | | |
| Distilled Water | 0.7 | 2.0 |
| Superunleaded gasoline | 0.6 | 4.7 |
| Humid aging resistance (90% relative humidity at 160° F./70° C.) | Poor | Fair to poor |

Preferably the free face of barrier layer 42 is slightly embossed with random striations to provide a pleasant feel when in contact with the skin. Preferably, microfastener layer 40 provides a VELCRO-type micro-loop outer face. Preferably, patches 30 and 32 provide a VELCRO-type micro-hook outer face for mating with the aforementioned micro-loop outer face. The extensive outer layer of the cold pack is provided with a VELCRO-type micro-loop surface, because it is considerably more comfortable than would be a VELCRO-type micro-hook surface when in contact with the skin.

The gel within compartment 22, in one form, is highly viscous aqueous dispersion of propylene glycol, preferably of the following formulation:

|  | Parts by Total Weight |
|---|---|
| Deionized water | 73.00 |
| Propylene Glycol | 24.50 |
| Hydroxyl Propyl Methyl Cellulose | 1.50 |
| Food Dye (FD & C) | 1.00 |

Ammonium Hydroxide, which is used as a processing aid in manufacturing this gel, may be present at less than one tenth of one percent (0.1%). All components are considered non-hazardous and all are commonly used in food, cosmetics and drugs.

Typical operation of the aforementioned cold pack is shown in FIG. 6. First the cold pack is stored in the freezing section of a refrigerator for a period sufficient to lower the temperature of the gel within the compartments to approximately the freezing temperature of water. When removed from the refrigerator, the cold pack is pressed into intimate contact with a part of the body requiring cryotherapy, in this case the lumbar region of the back. As shown, the cold pack is retained in the lumbar region at a patient's waist. Because of the wide area accessibility of the micro-fastener surface of cold pack 20, straps 26 are capable of maintaining the refrigerated cold pack securely in a preselected position on the patient's back. The cold pack of FIGS. 1 to 6 is sufficiently deformable, on a macro basis by virtue of its rectilinear articulations and on a micro basis by virtue of its slight elastomericity to permit bending in three dimensions through solid angles of from 30° to 90° and is sufficiently extensive to cover the major stress risors in the lumbar region of the back.

Although in this and the other embodiments illustrated herein, the straps have VELCRO-type fasteners at their extremities, it will be understood that in certain embodiments selected extremities of the straps are permanently fastened to the body of the cold pack herein disclosed.

The Cold Pack of FIGS. 8 to 12

The cold pack of FIGS. 8 to 12 is shown at 100 as comprising a plurality of cooling gel compartments 102 distributed between and defined by a pair of barrier layers of the type described in connection with FIG. 7. It will be observed that compartments 102 are distributed substantially throughout the extended area of the product and their combined areas are substantially equal to the extended area of the product as a whole. As shown on the face of the product in FIG. 8, these compartments are bounded by rectilinear seals or articulations 104 and 106 between the barrier layers. The relationships among these seals are such that seals 104 are parallel to each other and perpendicular to seal 106. At the back of the product, also distributed throughout this extended area, is a VELCRO-type fastener layer 108. Also constituting necessary components of the illustrated product is at least one strap 110, which includes an elastomeric band and a pair of end patches of the type described in connection with FIG. 5. Preferably, the extended fastener layer has a back surface that provides a VELCRO-type micro-loop texture. Preferably, each of the restricted patches on the straps has an outer surface that provides a VELCRO-type micro-hook texture. As in the embodiment of FIGS. 10 to 12, a polyurethane foam layer is interposed between the VELCRO-type micro-loop layer and the lower barrier layer.

Figure 12:
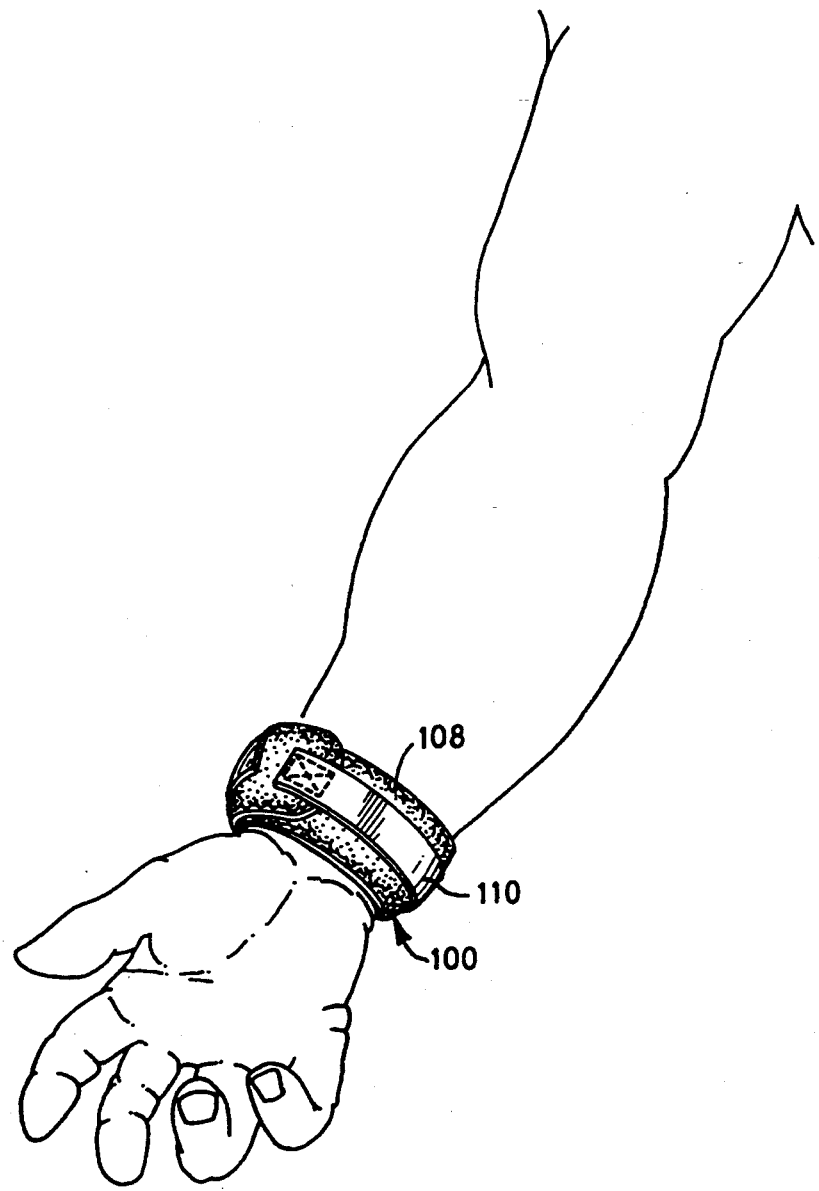
FIG. 12 is a perspective view of the cold pack of FIG. 8 in use.
Figure 13:
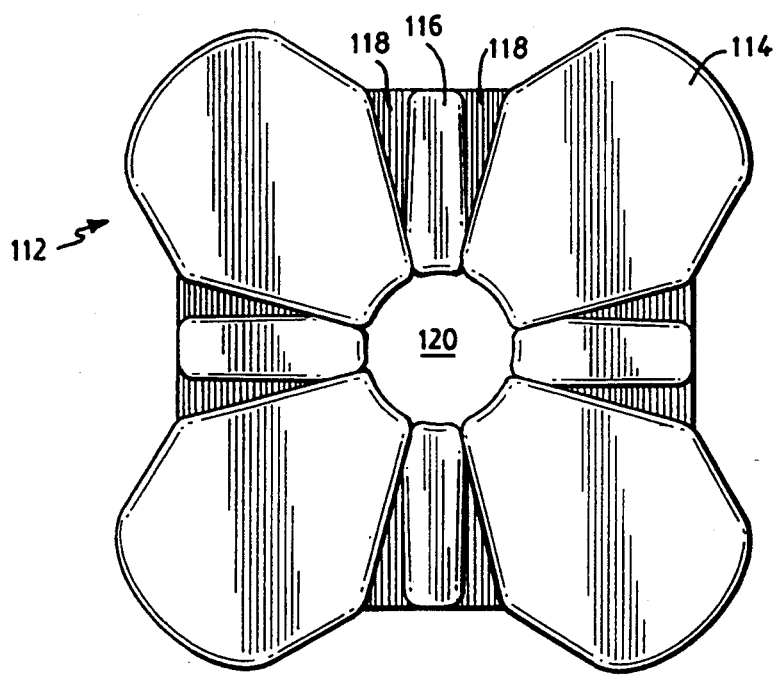
FIG. 13 is a top plan view of another cold pack for use on the knee or elbow in accordance with the present invention.
Figure 14:
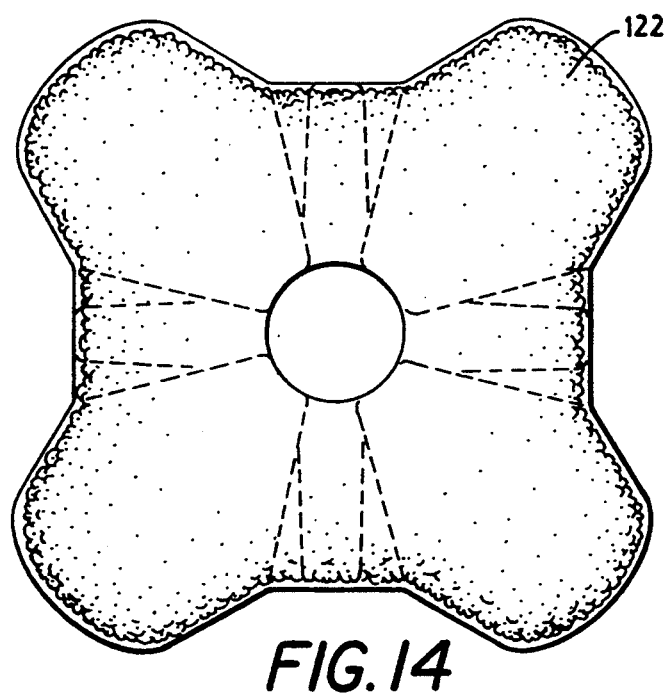
FIG. 14 is a bottom plan view of the cold pack of FIG. 13.
Figure 15:
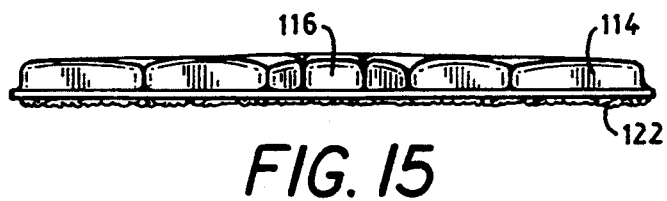
FIG. 15 is an edge view of the cold pack of FIG. 13.

The configurations of the profiles of the individual compartments, their geometrical interrelationships, and the configuration of the overall profile of the array of compartments are critical to the operation as illustrated in FIG. 12. Basically, this cold pack has a generally rectangular body with an elongated array of pairs of compartments. The arrangement is such that cold pack 100 may be snugly wrapped about the wrist, for example, with transversely related compartments comfortably resting against longitudinal areas of the wrist and longitudinally related compartments encircling the wrist.

The profiles of the compartments at the longitudinal extremities are bevelled to avoid points that might cause discomfort. When cold pack 100 is wrapped about the wrist, as shown in FIG. 12, its configuration may be set by strap 110, which mates at its opposite ends with the VELCRO-type micro-loop backing of the cold pack body. The cold pack of FIGS. 8 to 12 is rectilinearly articulated sufficiently to permit hinging and deformation in three dimensions through solid angles of from 30° to 90° and is sufficiently extensive to cover the stress risors in the wrist.

The Cold Pack of FIGS. 13 to 16

The cold pack of FIGS. 13 to 16 is shown at 112 as comprising a plurality of cooling gel compartments, four of which are of the type shown at 114, and four of which are of the type shown at 116. These compartments are defined by a pair of barrier layers of the type described in connection with FIG. 7. It will be observed that compartments 114, 116 are distributed substantially throughout the extended area of the product. As shown on the face of the product in FIG. 13, these compartments are distributed about a central axis and are separated by wedge-shaped flexible seals 118 between adjacent compartments. At the central axis is a central hole 120 which, in a related embodiment, is filled with a gel pack extention.

The relationships among these seals are such that the compartments can be cupped in three dimensions to receive an injured knee or elbow that projects through central hole 120. In other words, wedge shaped seals 118 permit compartments 114 and 116 to be folded three dimensionally into a cone-like configuration with hole 120 at its apex. Compartments 114 are clover-leaf-like in profile and orientation. Compartments 116, which are narrow, extend axially at 90° with respect to each other.

At the back of the product, also distributed throughout this extended area, is a VELCRO-type fastener layer 122. Also constituting necessary components of the illustrated product are a plurality of straps 124, 126, each of which includes an elastomeric band and a pair of end patches of the type described in connection with FIG. 5. Preferably, the extended fastener layer has a back surface that provides a VELCRO-type micro-loop texture. Preferably, each of the restricted patches on the straps has an outer surface that provides a VELCRO-type micro-hook texture.

Figure 16:
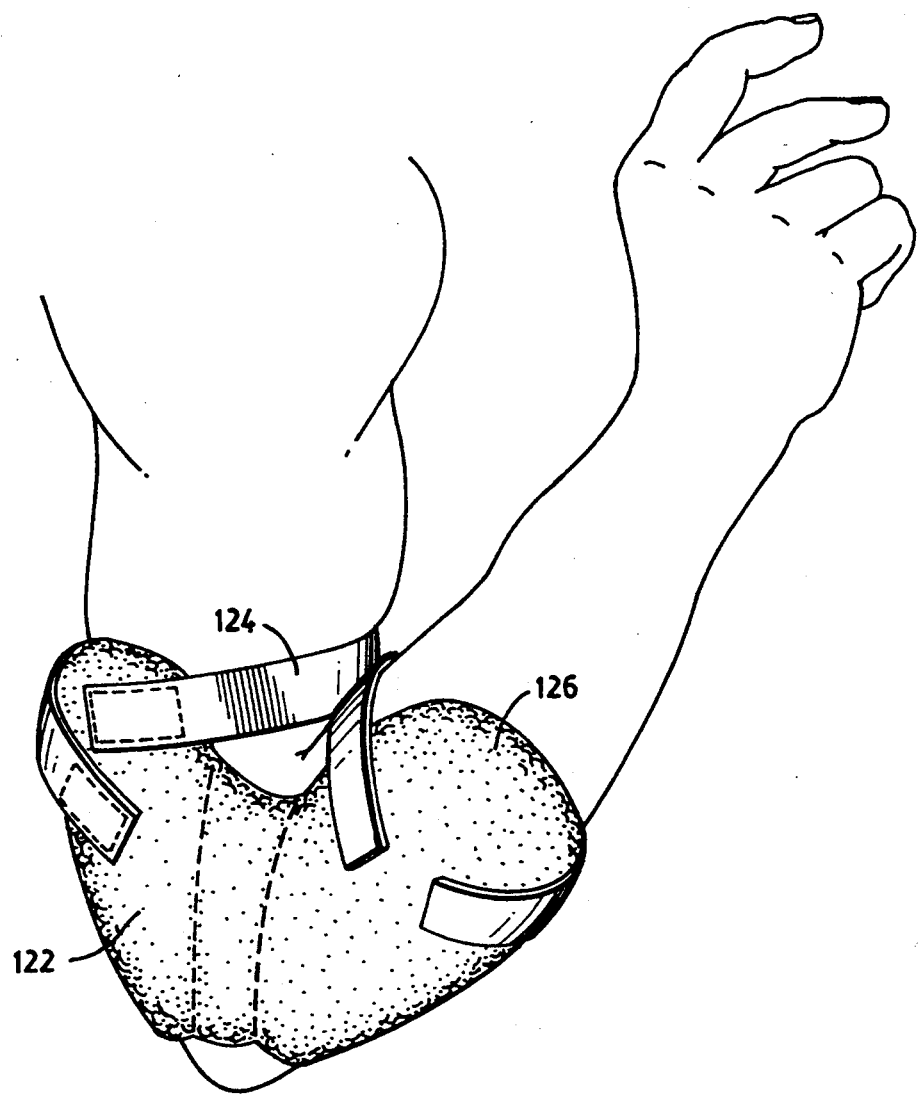
FIG. 16 is a perspective view of the cold pack of FIG. 13 in use.

The configurations of the individual profiles of the compartments, their geometrical interrelationships, and the configuration of the overall profile of the array of compartments are critical to the operation as illustrated in FIG. 16. Basically, this cold pack has a frustro-cusp shaped body with a recurring distribution of compartments separated by a plurality of seals about a geometrical center. The arrangement is such that the cold pack can be draped about the elbow as shown in FIG. 16, with the elbow projecting through hole 120 and with straps 124, 126 wrapped around the arm and the forearm and meshing at their opposite ends with the cold pack's VELCRO-type micro-loop backing. The cold pack of FIGS. 13 to 16 is sufficiently adjustable to permit hinging in three dimensions through solid angles of from 30° to 90° and is sufficiently extensive to cover the stress risors in the knee.

The Cold Pack of FIGS. 17 to 22

The cold pack of FIGS. 17 to 22 is shown at 128 as comprising a plurality of cooling gel compartments, various types of which are shown at 130, 132, 134 and 136, distributed between by a pair of barrier layers of the type described in connection with FIG. 7 and defined by intersecting rectilinear seals or articulations. It will also be observed that these compartments are distributed substantially throughout the extended area of the product. As shown on the face of the product in FIG. 17, these compartments are bounded by rectilinearly extending seals 138 between the barrier layers. The relationships among these seals are such that groupings of the compartments can be configured in three dimensions with respect to other groupings of these compartments. At the back of the product, also distributed throughout this extended area, is a VELCRO-type fastener layer 140. Also constituting necessary components of the illustrated product are a plurality of straps 140, 142, each of which includes an elastomeric band and a pair of end patches of the type described in connection with FIG. 5. Preferably, the extended fastener layer has a back surface that provides a VELCRO-type micro-loop texture. Preferably, each of the restricted patches on the straps has an outer surface that provides a VELCRO-type micro-hook texture.

Figure 21:
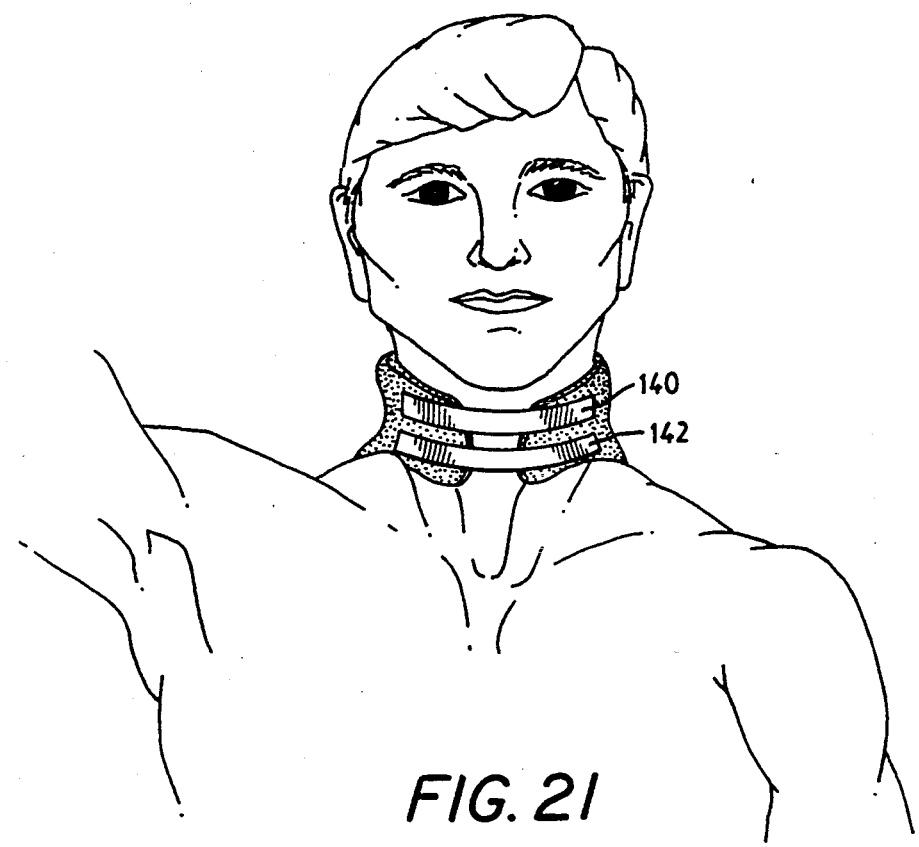
FIG. 21 is a front perspective view of the cold pack of FIG. 18 in use.
Figure 22:
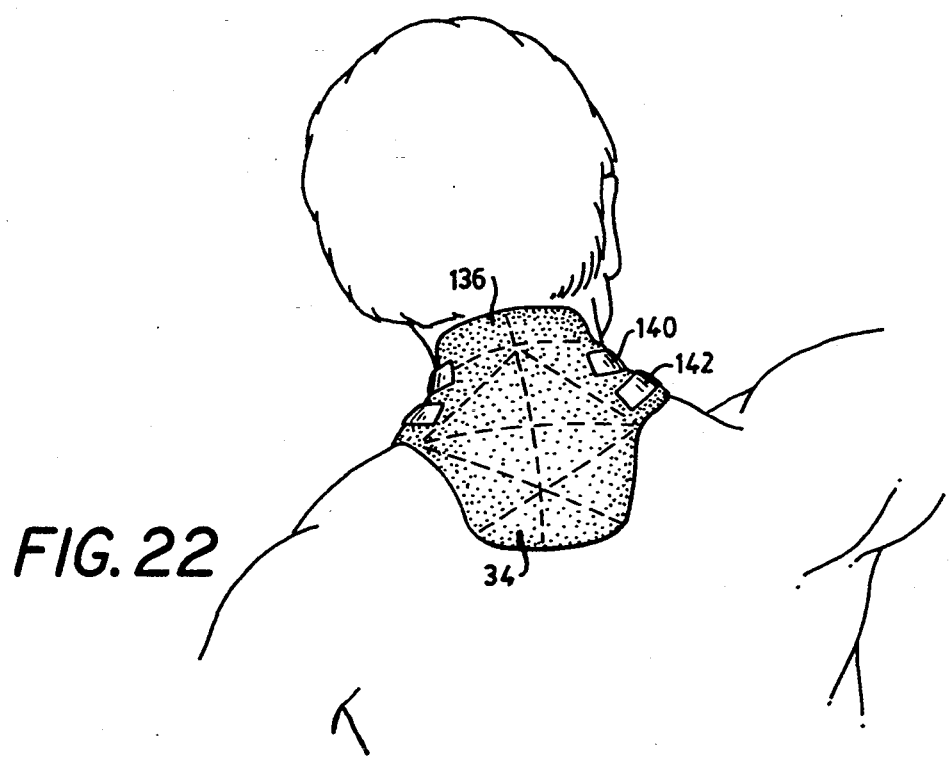
FIG. 22 is a back perspective view of the cold pack of FIG. 18 in use.
Figures 24, 26:
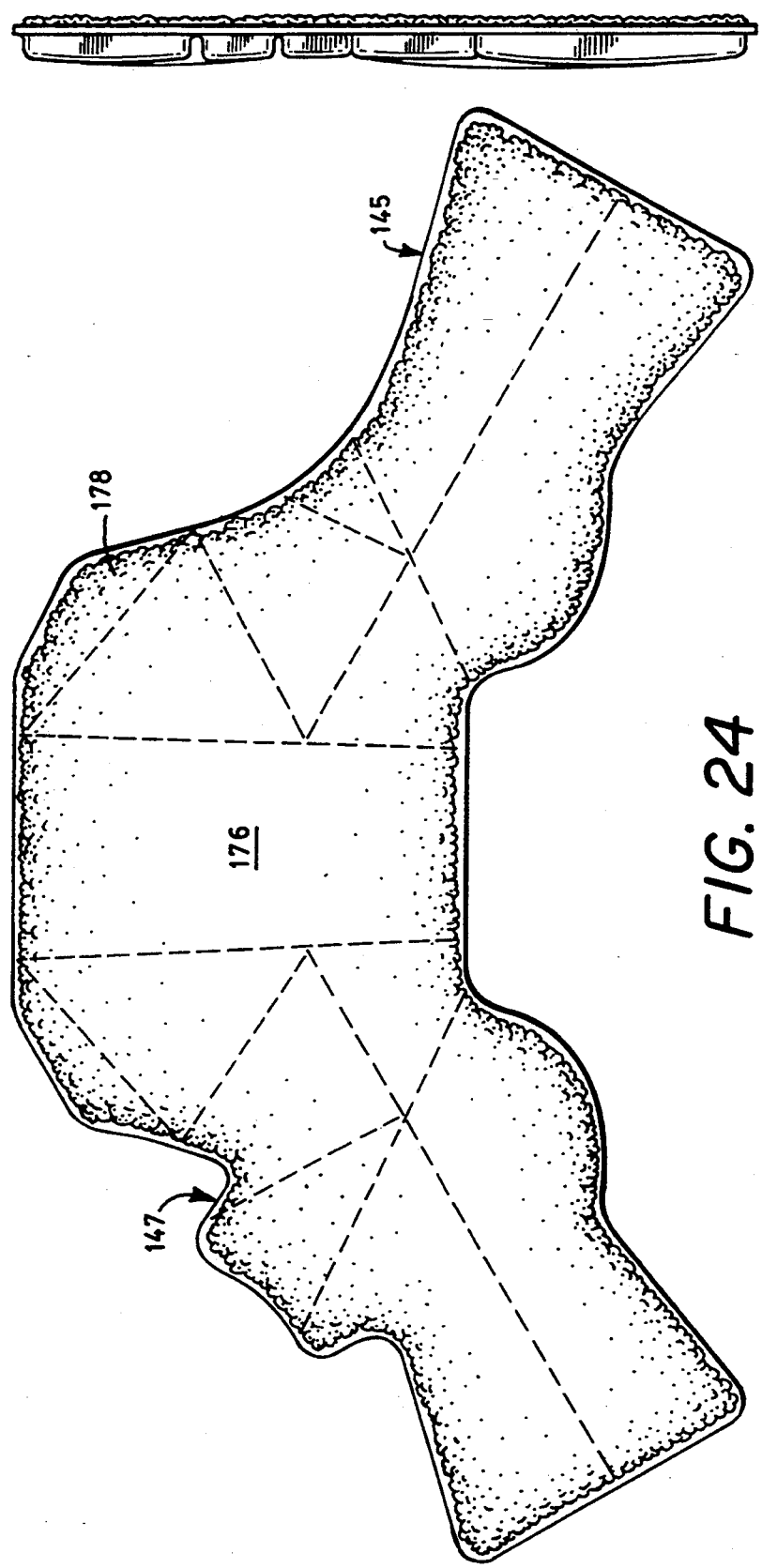
FIG. 24 is a bottom plan view of the cold pack of FIG. 23.
FIG. 26 is a side edge view of the cold pack of FIG. 23.

The configurations of the individual profiles of the compartments, their geometrical interrelationships, and the configuration of the overall profile of the array of compartments are critical to the operation as illustrated in FIGS. 21 and 22. Basically, this cold pack has a pair of cutward extensions 130, a pair of upward extensions 136, and a symetrical downwardly extending body including a plurality of tri-angularly shaped compartments 132, 134. As shown in FIGS. 17, 21 and 22, the body of cold pack 128 is designed to conform to the cervical region of the back with extensions 130 folded forwardly about the neck and extensions 136 directed upwardly to the skull. The triangular profile of the body compartments enable their groupings to conform to a range of different individualized anatomies.

The Cold Pack of FIGS. 23 to 27

The cold pack of FIGS. 23 to 27 is shown at 144 as comprising a pair of cooling gel compartment assemblages 145, 147, which in effect are substantially mirror images of each other. Assemblage 145 includes compartments 146, 150, 154, 158, 162, 166 and 170 Assemblage 147 includes compartments 148, 152, 156, 164, 168 and 172. These compartments are distributed between and defined by pairs of barrier layers of the type described in connection with FIG. 7. It will be observed that compartments 146, 150, 154, 158, 162, 166 and 170 are distributed substantially throughout assemblage 145; and compartments 148, 152, 156, 160, 164, 168 and 172 are distributed substantially throughout assemblage 147. As shown on the face of the product in FIG. 23, these compartments are bounded by rectilinearly extending seals 174 between the barrier layers. Assemblages 145 and 147 are separated from each other by a junction strip 176, which in one form is a fabric. The relationships among these seals are such that, when the foot rests on strip 176, assemblages 145 and 147 can be folded upwardly with groups of compartments 166, 170 and 168, 172 snugly about opposite sides of the metatarsal, groups of compartments 154, 158, 162 and 156, 160, 164 snugly about the ankle, and groups of compartments 146, 150 and 148, 152 snugly about the lower leg.

At the back of the product, distributed throughout the extended areas of assemblages 145 and 147 are a VELCRO-type fastener layers as shown at 178. Also constituting necessary components of the illustrated product are a plurality of straps 180, 182 and 184, each of which includes an elastic band and a pair of end patches of the type described in connection with FIG. 5. Preferably, the extended fastener layer has a back surface that provides a VELCRO-type micro-loop texture. Preferably, each of the restricted patches on the straps has an outer surface that provides a VELCRO-type micro-hook texture.

Figure 27:
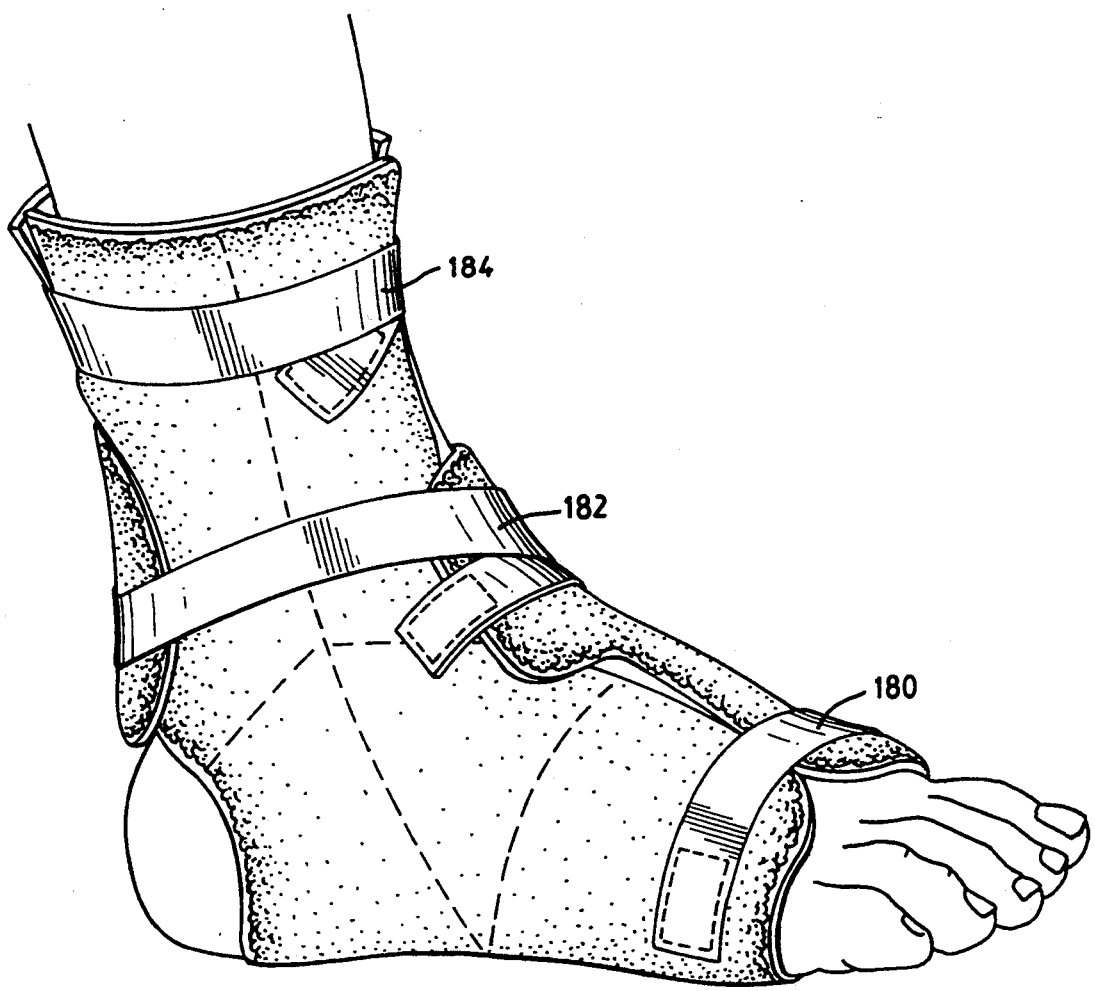
FIG. 27 is a perspective view of the cold pack of FIG. 23 in use.

The configurations of the individual profiles of the compartments, their geometrical interrelationships, and the configuration of the overall profile of the array of compartments are critical to the operation as illustrated in FIG. 27. These configurations enable an incremented conformation of substantially planar compartments folded in three dimensions. The cold pack of FIGS. 17 to 22 is sufficiently deformable to permit folding or hinging in three dimensions through solid angles of from 30° to 90° and sufficiently extensive to cover the stress risors at the junction of the neck and skull and the cervical region.

Figure 28:
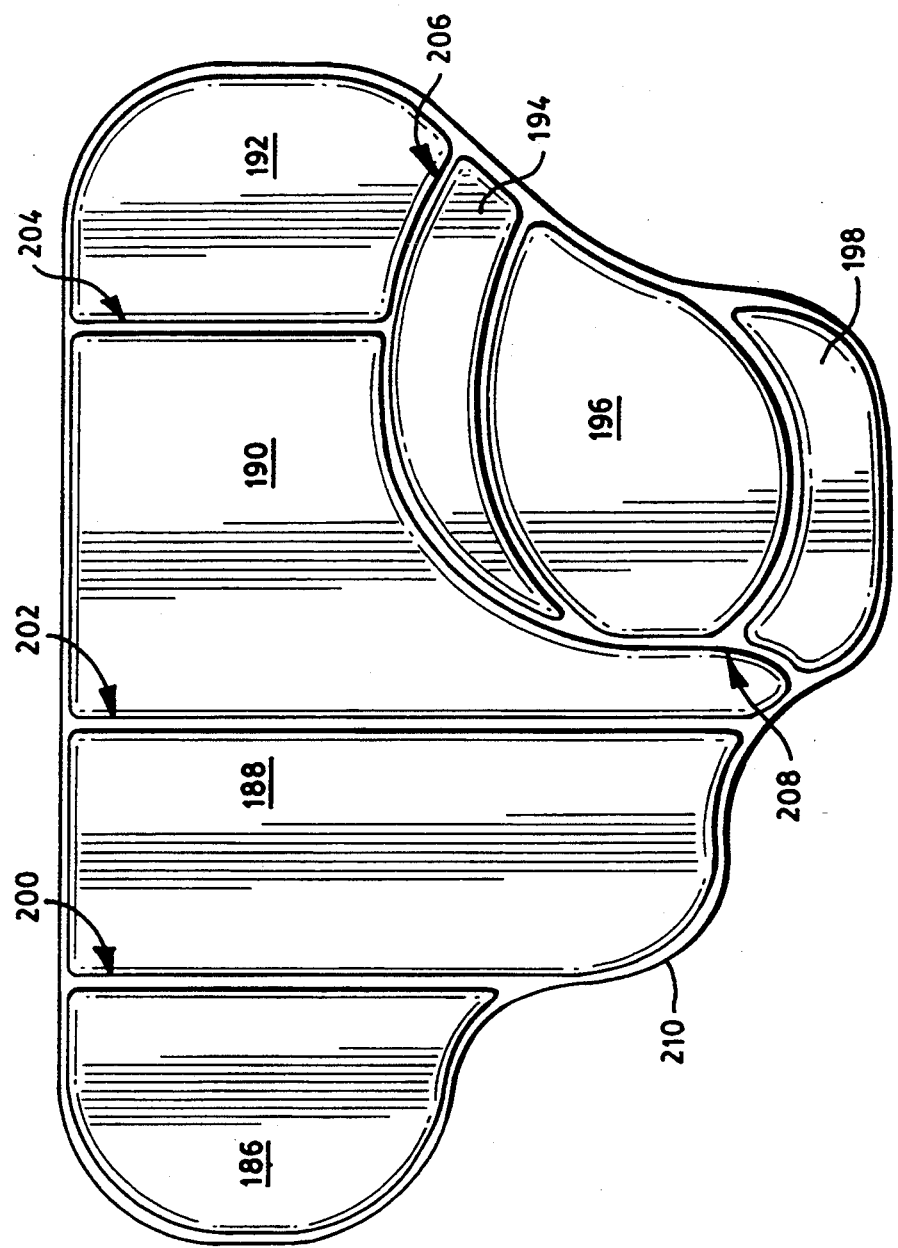
FIG. 28 is a top plan view of another cold pack of the present invention.

The Cold Pack of FIG. 28

The cold pack of FIG. 28 is shown comprising a plurality of cooling gel compartments of various types which are shown at 186, 188, 190, 192, 194, 196, and 198. These compartments are defined by a pair of layers of the type described in connection with FIG. 7. It will be observed that these compartments are distributed substantially throughout the extended area of the product. As shown, compartments 186, 188, 190 and 192 are separated or articulated by intersecting rectilinear seals 200, 202 and 204. Compartments 194, 196, and 198 are separated solely by angular seals 200, 202, 204, and 206.

The relationship between these seals is such that compartments 190 and 192 form two adjoining angular seals 206 and 208, separating compartments 194, 196, and 198, that are convex with respect the rectilinear intersections formed by rectilinear seals 200, 202 and 204. The unseen underlying face of each compartment shown is covered by a thin layer of plastic and the plurality of compartments may be configured in three dimensions such that each plastic surface seats snugly ever a portion of the right half of the head.

Compartments 194 and 196 are designed to rest snugly over the eye and eyebrow, respectively. Compartment 190 is designed to rest snugly directly beneath the anatomical resting surface of compartment 194, above the cheek. Compartments 186, 188, 190 and 192 are designed to fit snugly over an anatomical surface, adjoining the combined anatomical surfaces of compartments 194, 196 and 198, which contains frontal, pareital, sphenoid and temporal portions of the head.

In a closely related embodiment, the shown face of each compartment 186, 188, 190, 192, 194, 196 and 198 may also be covered with a thin layer of plastic and the plurality of compartments may be configured in three dimensions to conform to the left half of the face with the corresponding compartment-anatomical structure conformation described above. Similarly, both sides of the cold pack may be covered with a thin layer of plastic and the plurality of the compartments may be configured to conform to both halves of the face with the corresponding compartment-anatomical structure conformation described above.

In another related embodiment, compartments 194 and 196 are not present in the cold pack and compartments 186, 188, 190, 192, 198 as well as boundary seal 210 enclose an open space substantially the same shape and combined area the faces of compartments 194 and 196 encompass. The cold pack may be configured into three dimensions such that the open space conforms over the eye and eyebrow and compartments 186, 188, 190, 192 and 198 rest on the corresponding anatomical surfaces of the head described above.

At the back of the product, also distributed throughout this extended area, is a VELCRO-type fastener layer. Also constituting necessary components of the illustrated product is at least one detachable cranial strap which includes an elastomeric band and a pair of end patches of the type described with FIG. 5. Preferably, each of the restricted patches on the straps has an outer surface that provides a VELCRO-type micro-hook texture.

Figure 29:
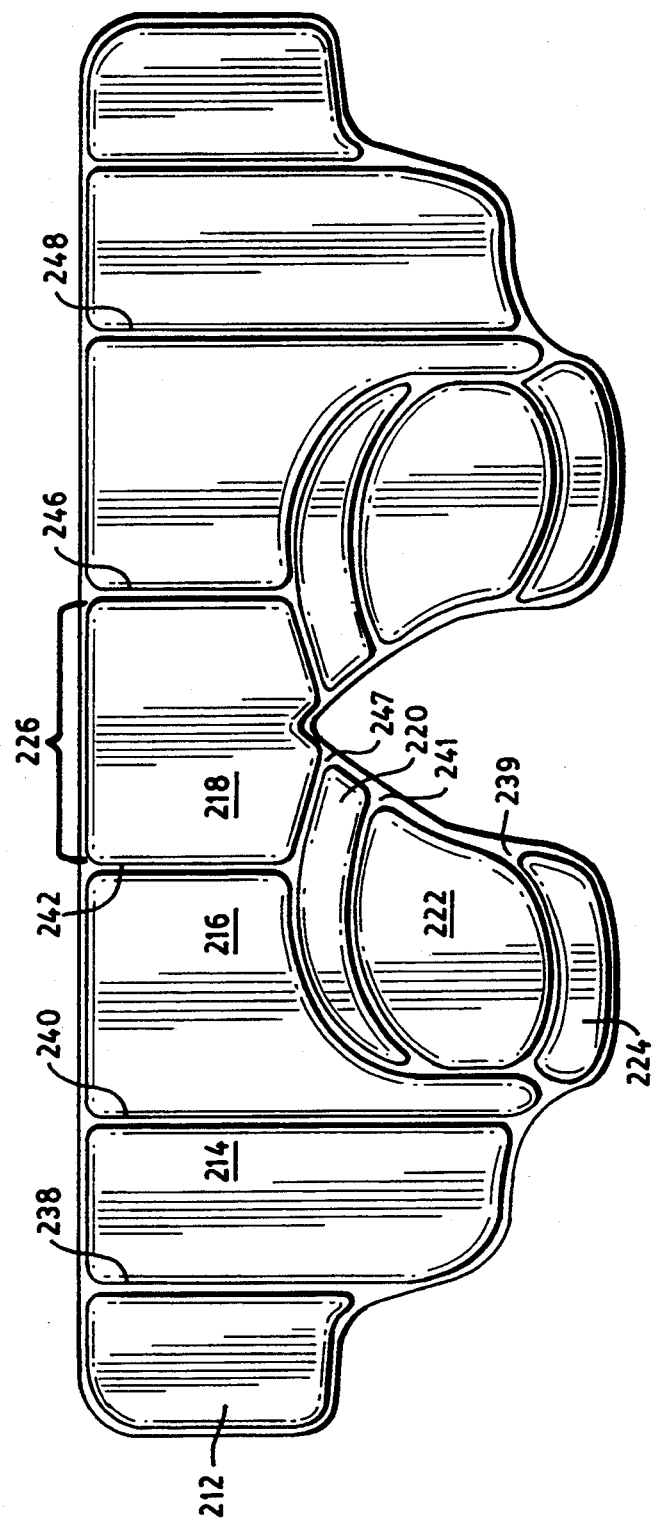
FIG. 29 is a top plan view of another cold pack of the present invention.

The configurations of the individual profiles of the compartments, their geometrical interrelationships, the configuration of the overall profile of the compartments are critical to the operation as illustrated in FIG. 29. Basically, this cold pack has a relatively small irregularly shaped body with a recurrent distribution of compartments which are designed to rest about the upper half of the face.

The Cold Pack of FIG. 29

The cold pack of FIG. 29 is shown comprising a plurality of cooling gel compartments of various types shown at 212, 214, 216, 226, 228, 218 and 230. These compartments are defined by a pair of layers of the type described with FIG. 7. It will be observed that these compartments are distributed substantially throughout the extended area of the product. As shown, compartments 212, 214, 216, 218, 220, 222 and 224 are separated or articulated by intersecting rectilinear seals 238, 240, 242, 244 and 246. Compartments 226, 228, 230, 232 234 and 236 are separated solely by angular seals 231, 233 and 235.

The relationship between these seals is such that the seals may be configured in three dimensions in such manner that their combined adjoining cooling surfaces rest snugly against substantially the same anatomical resting surfaces of the compartments of the right and left models of the cold pack described in FIG. 28. It will be observed that the cooling surfaces of the compartments are covered by a thin lawyer of plastic and that the plurality of compartments are distributed in a mirror-like configuration about a plane parallel to rectilinear seals 212, 214, 216, 218, 222 and 224 intersecting the midpoint of boundary seal portion 226.

In a related embodiment, compartments 226, 228 and 232 and 234 may be absent, forming open spaces and the cold pack may be configured in three dimensions over the eyes and eyebrows in a substantially similar manner described in FIG. 28.

At the back of the product, also distributed throughout the extended area of the compartments, is a VELCRO-type fastener layer. Also constituting necessary components of the illustrated product is at least one detachable cranial strap which includes an elastomeric band and a pair of end patches of the type described with FIG. 5. Preferably, each of the restricted patches on the straps has an outer surface that provides a VELCRO-type micro-hook texture.

The configurations of the individual profiles of the compartments, their geometrical interrelationships, the configuration of the overall profile of the compartments are critical to the operation as described above. Basically, this cold pack has a mask-shaped body with a recurrent distribution of compartments, separated by a plurality of rectilinear and angular seals, and is designed to cover and anatomical surface containing both eyes.

Figure 30:
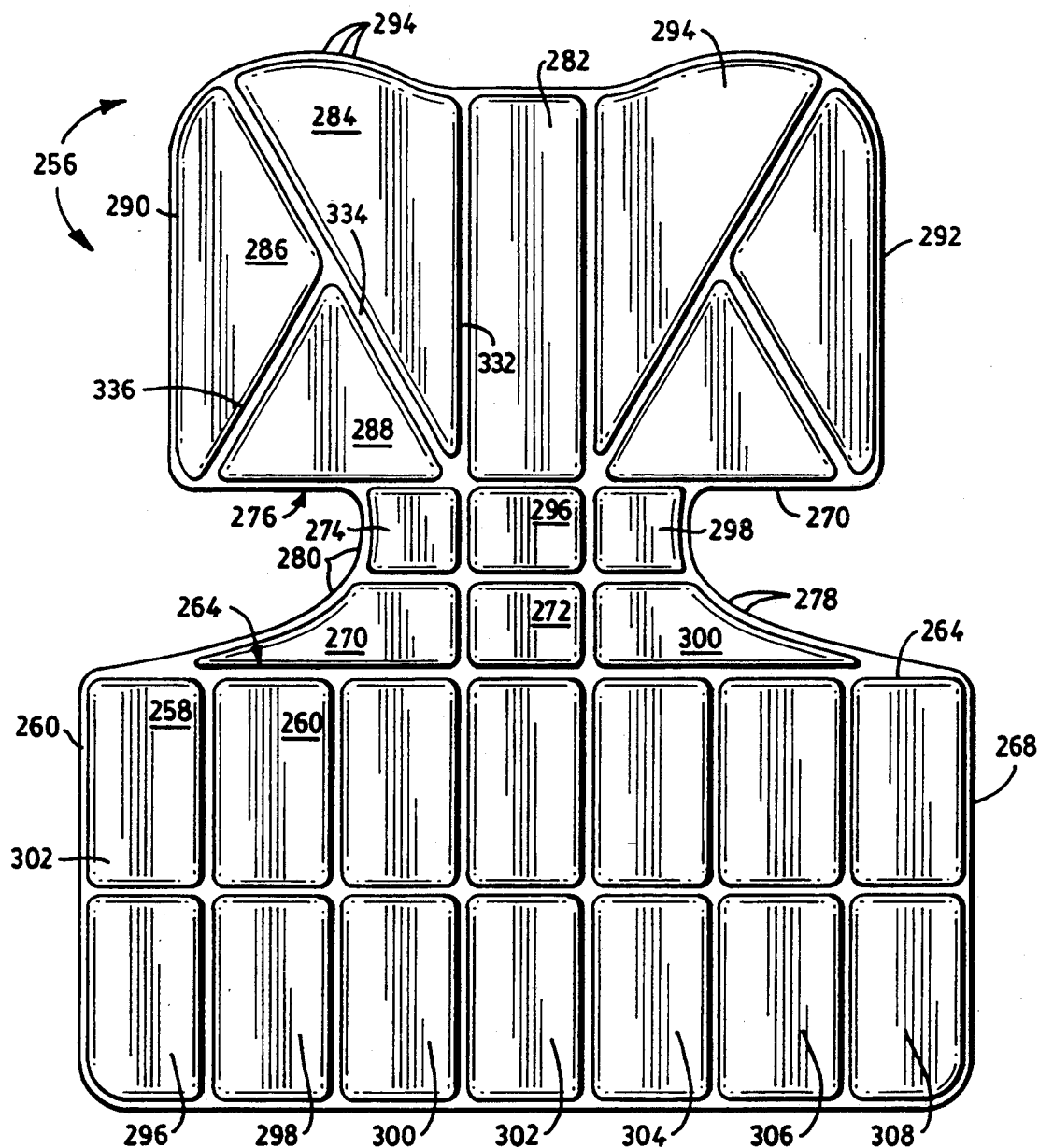
FIG. 30 is a top plan view of another cold pack of the present invention.
Figure 31:
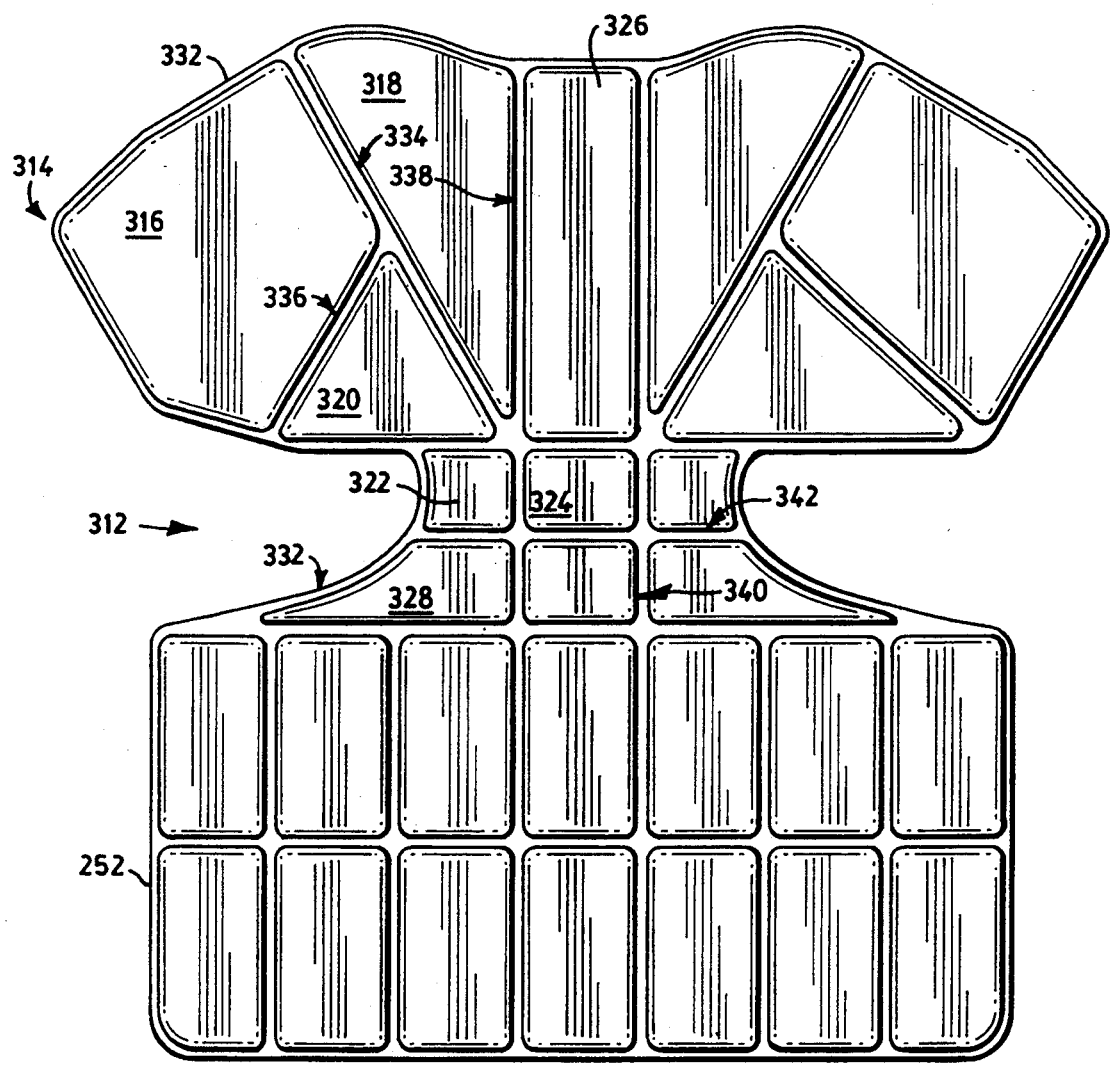
FIG. 31 is a top plan view of another cold pack of the present invention.

The Cold Packs of FIGS. 30-31

The cold pack of FIG. 30 is shown comprising a plurality of cooling gel compartments distributed into three adjoining assemblages 252, 254, and 256. These compartments are defined by a pair of layers of the types described in connection with FIG. 7. It will be observed that these compartments are distributed substantially throughout the extended area of the product. As shown, assemblage 252 comprises of substantially rectangular compartments 258 and 260, separated by intersecting rectilinear seals 296, 298, 300, 302, 304, 306 and 308. The cooling surfaces of these compartments extend over an area bounded by a border seal defined by two pairs of parallel rectilinear seals 262, 264 and 266, 268 each seal being angular at each end, arranged in a rectangular-like fashion such that the angular portions of the seals form four parabolic corner edges concave with respect to each other.

Assemblage 254 comprises of compartments of the type shown at 270, 272, and 274 which are separated by intersecting rectilinear seals 296, 298 and 300. These compartments lie within a border seal defined by parallel rectilinear seals 264, and 276 joined by two angular seals 278, and 280.

Assemblage 256 comprises of triangular, rectangular, and multilateral compartments of the type shown at 282, 284, 286 and 288 which are separated by rectilinear seals 332, 334, and 336. The cooling surfaces of these compartments extend over an area bounded by a border seal defined by rectilinear seals 290 and 292, each seal having two angular ends, which are joined by rectilinear seal 276 and angular seal 294. It will be observed that the compartments of assemblages 252, 254 and 256 form mirror images of each other about a tangent plane parallel to rectilinear seals 300 and 302 and intersecting the midpoint of rectilinear seals 262, 310, 264, and 276.

The relationship among these seals in assemblages 252, 254 and 256 is such that the seals may be configured in three dimensions in such manner that their combined adjoining cooling surfaces rest snugly over an anatomical resting surface covering the anterior, posterial, and medial regions of the shoulder. Assemblages 252 and 254 are designed to fit snugly over an anatomical surface covering the anterior, medial and posterior regions of the trapezius muscles. Assemblage 256 is designed to rest snugly over the anterior, medial, and posterior portions of the deltoid muscles.

In a related embodiment, as shown by FIG. 31 assemblages 252 is adjoined by assemblages 314 and 312 which are comprised of a plurality of compartments of types 316, 318, 320, 326, 328, 324, and 322. As shown, the compartments comprising assemblage 314 are separated by rectilinear seals of the types shown at 336 and 338 and the compartments comprising assemblage 312 are separated by rectilinear seals of the type shown at 340 and 342. These compartments extend over an area bounded by multilateral angular seal 332.

The relationship between the seals in the compartments comprising assemblages 312 and 314 is that they may be configured in three dimensions, along with assemblage 252, with a substantially similar compartment-anatomical representation described in the previous embodiment.

At the back of each embodiment, also distributed throughout the product's extended area, is a VELCRO-type fastener layer. Also constituting necessary components of the illustrated product are detachable thoraic and brachial straps. Each strap includes an elastomeric band and a pair of end patches of the type described with FIG. 5. Preferably, each of the restricted patches of the straps has an outer surface that provides a VELCRO-type micro-hook texture.

The configurations of the individual profiles of the compartments, their geometric relationships, the configuration of the overall profile of the compartments are critical to the operation described above. Basically, this cold pack has a multilaterally shaped body with a recurrent distribution of compartments which are designed to rest snugly over the shoulder.

Figure 32:
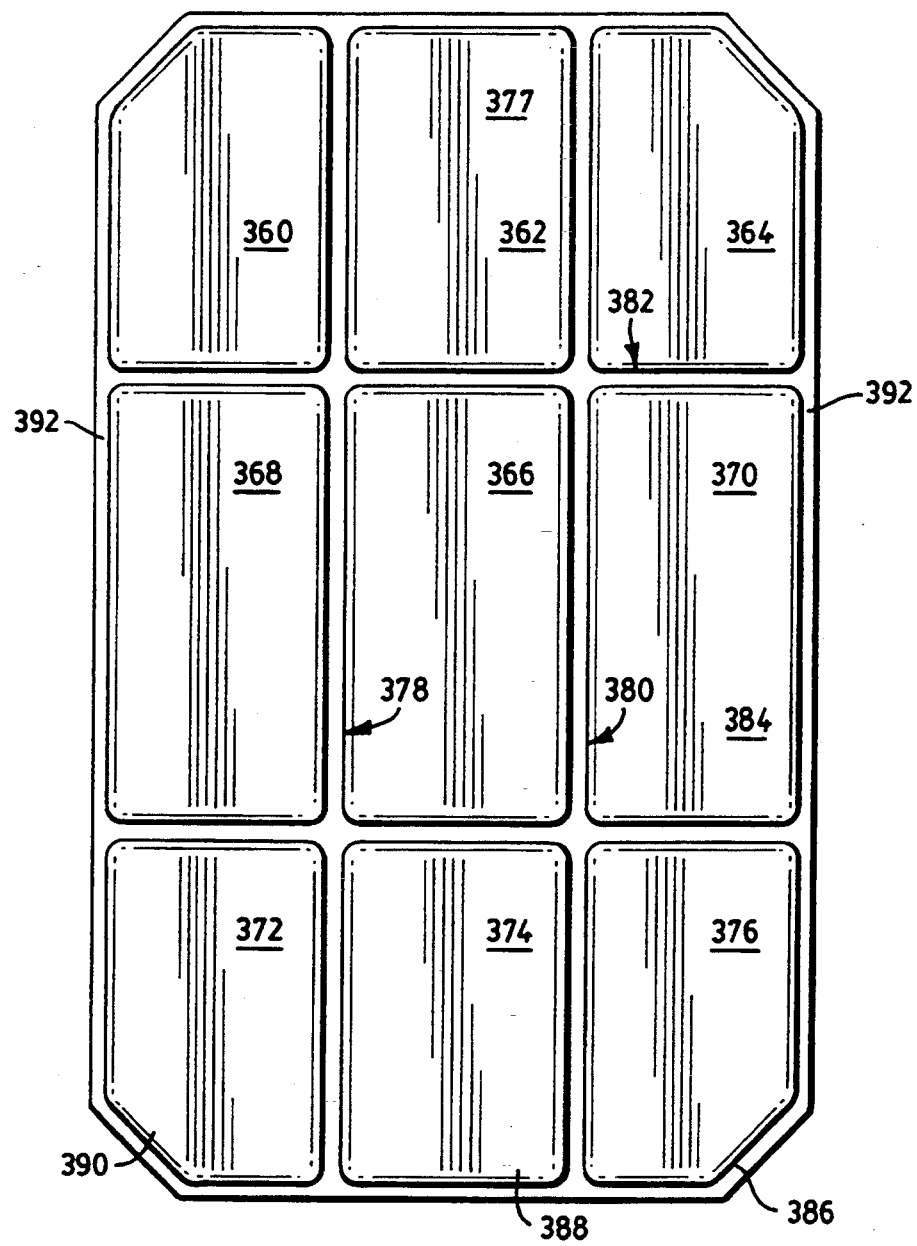
FIG. 32 is a top plan view of another cold pack of the present invention.
Figure 33:
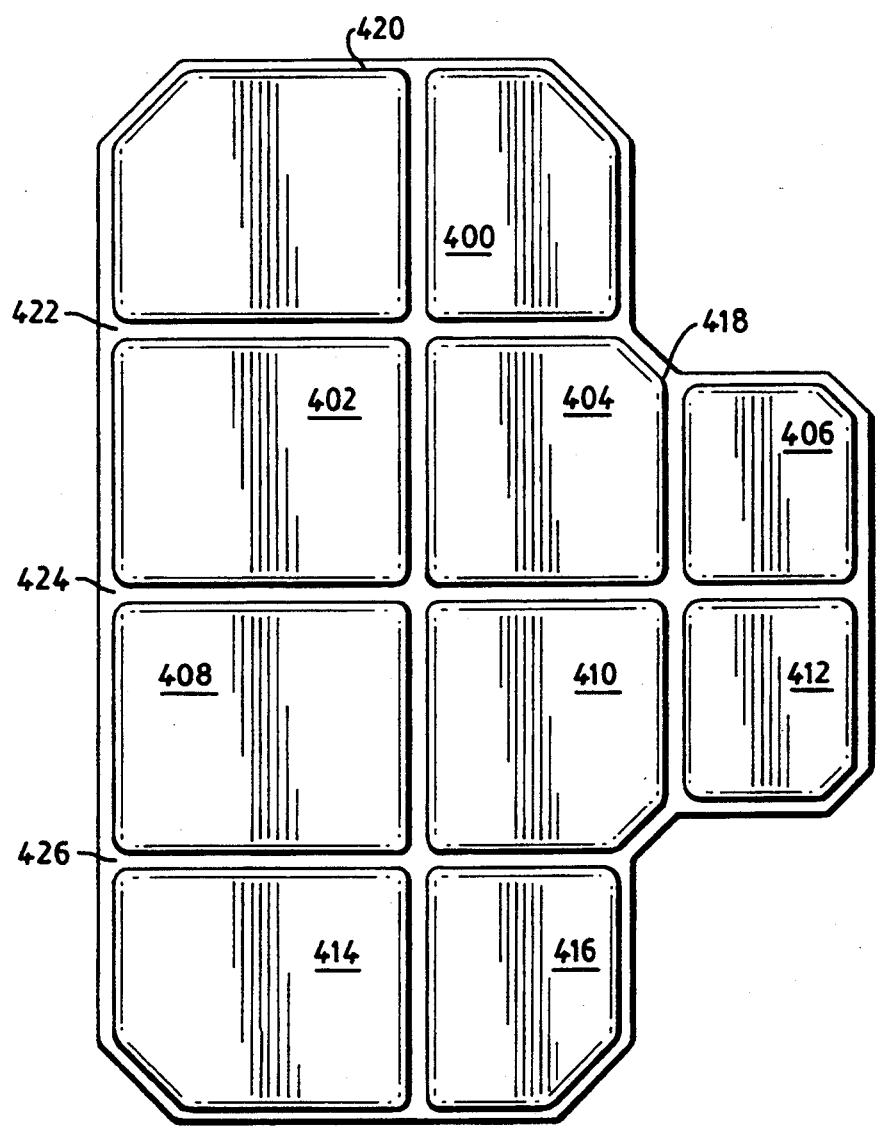
FIG. 33 is a top plan view of another cold pack of the present invention.

The Cold Packs of FIGS. 32–33

The cold pack of FIG. 32 is shown comprising a plurality of cooling gel compartments of various types which are shown at 360, 362, 366 368, 370, 374 and 376. These compartments are defined by a pair of layers of the type described in connection with FIG. 7. It will be observed that these compartments are distributed substantially throughout the extended area of the product. As shown, these compartments are separated or articulated by intersecting seals 378, 380, 382 and 384. These compartments lie within a border seal defined by four pairs of parallel rectilinear seals 386, 388, 392, and 390, arranged into an octagon such that the linking seals form approximately 45° angles. The relationships among these seals is that the seals may be configured in three dimensions in such manner that their combined adjoining cooling surfaces fit snugly over an anatomical surface covering anterior, medial, and posterior regions of a thigh.

In a related embodiment shown at FIG. 33, a plurality of compartments of various types shown at 398, 400, 402, 404, 406, 408, 410, 412, 414, and 396 are separated by rectilinear seals 418, 420, 422, 424 and 426. These seals may be configured in three dimensions in such manner that they also rest snugly over an anatomical resting surface containing the anterior, medial, and medial regions of the thigh.

At the back of the product, also distributed throughout the extended area of the compartments, is a VELCRO-type fastener layer. Also constituting necessary components of the illustrated product is at least one strap which includes an elastomeric band and a pair of end patches described with FIG. 5. Preferably, each of the restricted patches on the straps has an outer surface that provides a VELCRO-type micro-hook texture.

The configurations of the individual profiles of the compartments, their geometric interrelationships, the configuration of the overall profile of the compartments are critical to the operation as described above. Basically, this cold pack has a recurrent distribution of compartments, separated by a plurality of rectilinear seals, which are designed to fit snugly about the thigh.

Figure 34:
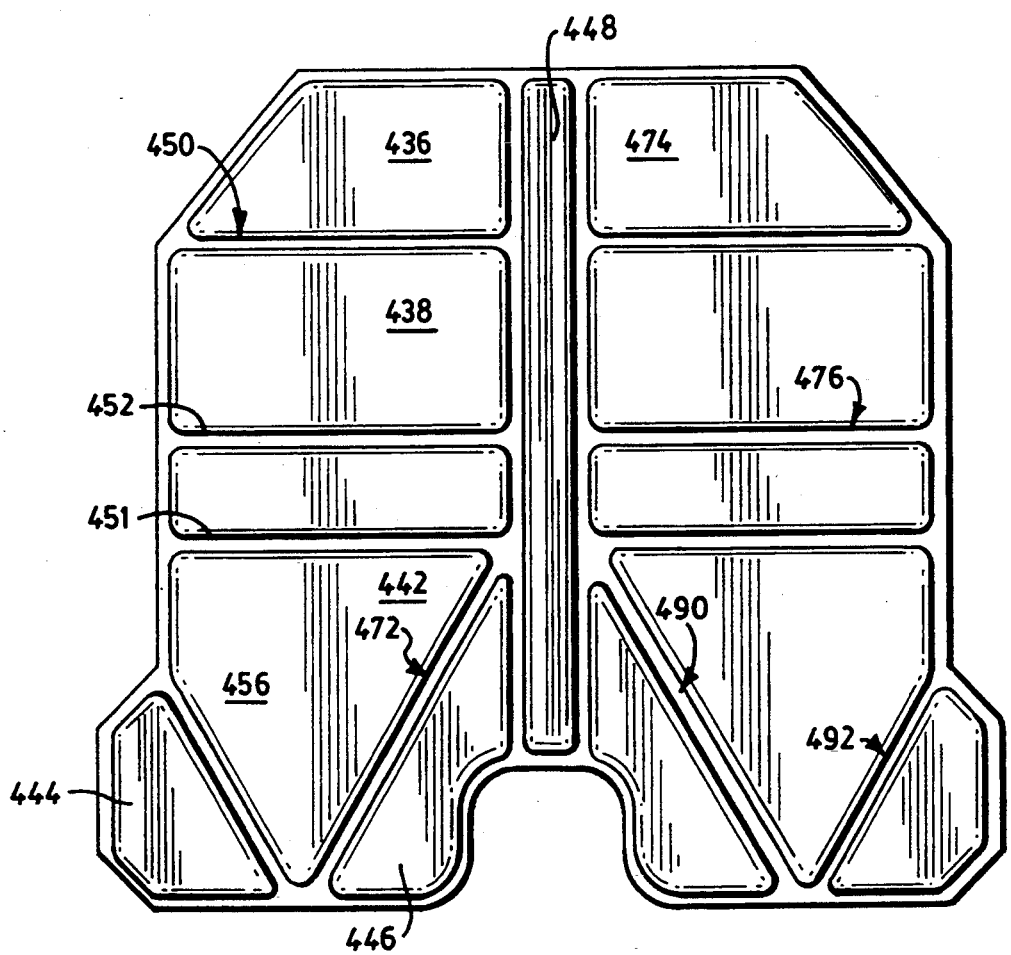
FIG. 34 is a top plan view of another cold pack of the present invention.

The Cold Pack of FIG. 34

The cold pack of FIG. 34 is shown comprising a plurality of cooling gel compartments of various types which are shown at 436, 438, 440, 442 444, 446 and 448. These compartments are defined by a pair of layers of the type described in connection with FIG. 7. It will be observed that these compartments are distributed substantially throughout the extended area of the product. As shown, the compartments are arranged in groups symmetrical about rectangular compartment 448. The compartments are separated or articulated by intersecting rectilinear seals 450, 452, 454, 456, 472, 474, 476, 478, 490 and 492. The relationship between these seals is such that the seals may be configured in three dimensions in such manner that their combined adjoining cooling surfaces rest snugly over an anatomical resting surface containing the posterior pelvic region.

Compartment 448 is designed to fit snugly over the lumbar and thoracic vertebrae. Compartments 436, 438, 440, 442, 444, and 446 are designed to fit snugly over the adjoining right half of the posterior pelvic region, and compartments 460, 462, 464, 466, 468 and 470 are designed to fit over the left half of the posterior pelvic region.

At the back of the product, also distributed throughout the product's extended area, is a VELCRO-type fastener layer. Also constituting necessary components of the illustrated product is at least one detachable strap which includes an elastomeric band and a pair of patches described with FIG. 5. Preferably, each of the restricted patches of the straps has an outer surface that provides a VELCRO-type micro-hook texture.

The configurations of the individual profiles of the compartments, their geometric relationships, the configuration of the overall profile of the compartments are critical the operation as described above. Basically, this cold pack has a recurrent distribution of compartments, separated by a plurality of rectilinear seals, which are designed to fit snugly over the posterior pelvic region.

Figure 35:
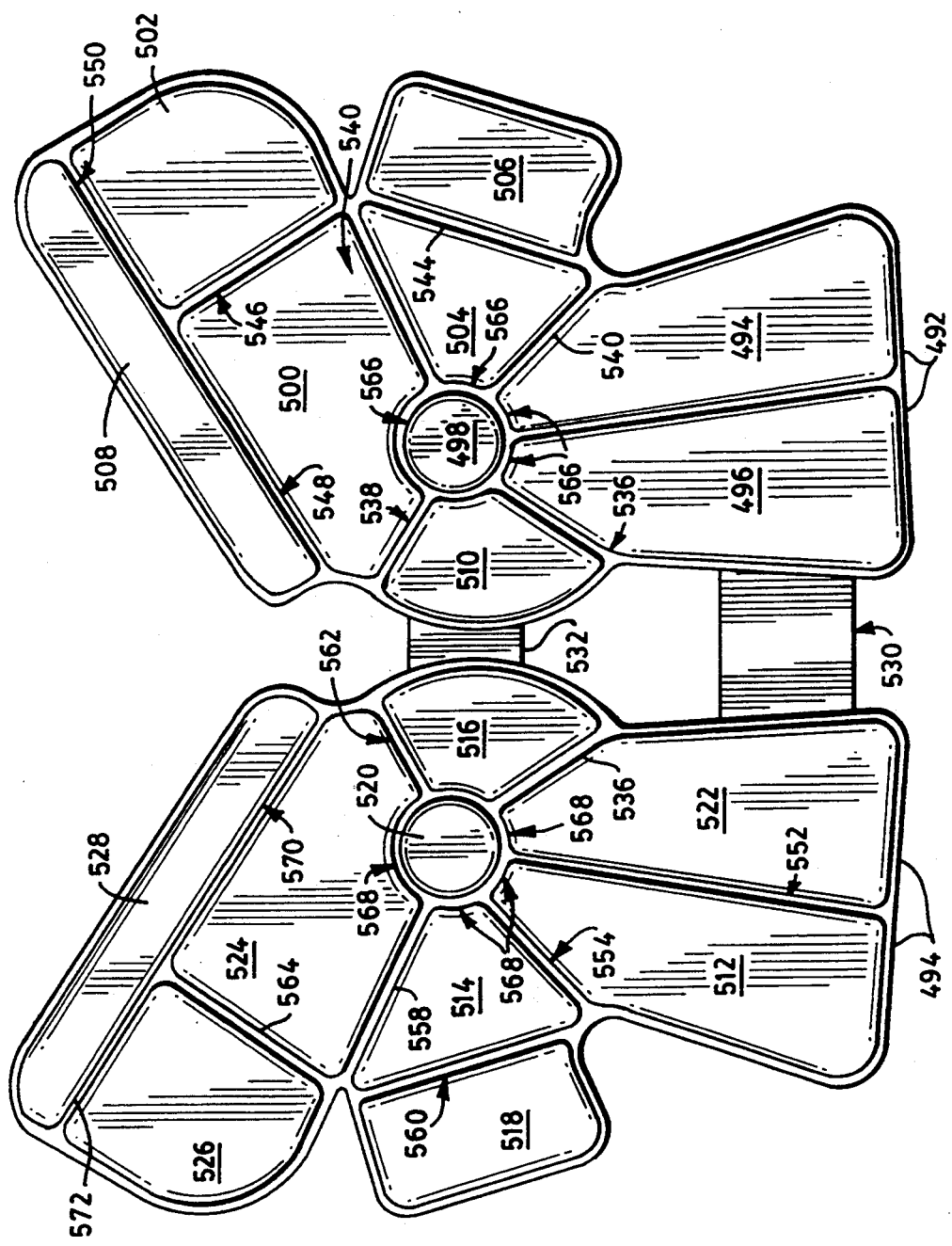
FIG. 35 is a top plan view of another cold pack of the present invention.

The Cold Pack of FIG. 35

The cold pack of FIG. 35 is shown comprising a pair of cooling gel compartment assemblages 492 and 494 which in effect are substantially mirror images of each other and separated by elastic straps 530 and 532. Assemblage 492 includes compartments 494, 496, 498, 500, 502, 504, 506, 508, and 510. Assemblage 494 includes compartments 512, 514, 516, 518, 520, 522, 524, 526, and 528. These compartments are distributed between and defined by pairs of barrier layers of the type described with FIG. 7. The displayed surfaces of the assemblages are covered with a thin insulating layer of plastic. As shown, compartments 494, 496, 498, 500, 502, 504, 506, 508 and 510 are distributed substantially throughout assemblage 492; and compartments 512, 514, 516, 518, 520, 522, 524, 526, and 528 are distributed substantially throughout assemblage 494. The compartments of assemblage 492 are separated by rectilinear seals 534, 536, 53S, 540, 542, 544, 546, 548 and circular seal 566; and the compartments of assemblage 494 are separated by rectilinear seals 550, 552, 554, 556, 558, 560, 562 and 564 and circular seal 568.

The relationship among these seals is such that the seals may be configured in three dimensions such that their adjoining cooling surfaces rest snugly over an anatomical surface covering the medial and lateral portions of the foot.

Assemblages 492 and 494 may conform to the lateral and medial sides of the right foot or the medial and lateral sides of the left foot, respectively. If the right foot conformation is chosen, compartments 500, 502, 508, and 510 are designed to fit snugly over the portions of the foot covering the culcaneus, cuboid and metatarsals while compartments 494, 496, 498, 504 and 506 are designed to fit snugly over the ankle and adjoining lateral regions. Further, compartments 516, 524, 526, and 528 are designed to seat snugly over the calcaneus, navicular, cuneiforms and metatarsals and compartments 512, 514, 518, 520 and 522 are designed to fit snugly over the ankle and adjoining medial regions about the ankle joint. Similarly, assemblages 492 and 494 may rest over the medial and lateral portions of the left foot with a corresponding compartment-anatomical structure conformation as described above.

At the back of the product, distributed throughout the extended areas is a VELCRO-type fastener layer. Also constituting necessary components of the illustrated product are at least three detachable straps. Each strap includes an elastomeric band and a pair of end patches of the type described with FIG. 5. Preferably, each of the restricted patches on the straps has an outer surface that provides a VELCRO-type micro-hook texture.

The configurations of the individual profiles of the compartments, their geometrical interrelationships, the configuration of the overall profile of the compartments are critical to the operation described above. Basically, this cold pack has two multilaterally shaped assemblages which are separated by a pair of straps and is designed to rest snugly about the medial and lateral portions of the foot.

General Operation

In operation, each of the illustrated cold packs is refrigerated for a sufficiently long period to reduce its temperature to from 15 to 35 degrees F. The composition is such that throughout this range, the gel within the compartments remains fluid. The compartments are hinged to each other by intersecting articulations that are defined by hermetic seals in the barrier layers that form the walls of the compartments. The intersecting articulations are sufficiently wide and particularly shaped to permit the cold pack to be conformed in relatively macro increments to the general contour against which it is being pressed. The fluid condition of the gel and the compliance of the compartments permit the cold pack to be conformed in relatively micro-increments to the specific contour against which it is being pressed. An extensive micro-fastener stratum is superimposed on a large part of the cold pack spanning a plurality of the compartments. Elastomeric straps with restricted micro-fastener patches are stretched about the body. When the micro-fastener patches and stratum are mated, the cold pack is retained in predetermined position, under predetermined pressure, for a predetermined period until conveniently removed.

What is claimed is:

1. A therapeutic cold pack for temporary affixation at an operating temperature to a restricted area of the human body, said operating temperature being lower than the normal temperature of the human body, said cold pack including a pair of opposed faces having an extended area, said cold pack comprising:
   (a) a pair of hermetic barrier layers that are heat sealed together throughout a plurality of intersecting articulations defining a plurality of compartments;
   (b) a refrigerant gel contained within said compartments, said refrigerant gel having a high specific heat such that after becoming cooled it absorbs a large quantity of heat while undergoing phase change on heating;
   (c) said plurality of compartments being arranged in a pair of assemblages, each being a mirror image of the other, said assemblages being separated from each other by a central junction strip, formed of a fabric;
   (d) adjoining ones of said compartments being hinged to each other along axes, certain of said axes intersecting others of said axes;
   (e) said compartments being adapted to be folded with respect to each other along said intersecting axes into a configuration that is snugly seated against an irregular three dimensional anatomical surface;
   (f) a restricted fastener area on the back of said cold pack extending substantially throughout said extended area;
   (g) a plurality of straps each having elongated restricted fastener areas at its opposite ends;
   (h) said restricted fastener areas of said strap being engageable with any part of said extended fastener area on said cold pack to secure said compartments in said configuration;
   (i) said gel being fluid at its operating temperature;
   (j) said restricted fastener area and said extended fastener area including mating surfaces;
   (k) said mating surfaces including micro-loop surfaces and micro-hook surfaces;
   (l) said hermetic barrier layers being composed of polyurethane sheet;
   (m) said refrigerant gel including an aqueous dispersion of ethylene glycol;
   (n) said plurality of compartments having a combined anatomical surface area that is substantially greater than the combined surface area of said intersecting articulations;
   (o) said articulations being sufficiently wide to permit limited skew orientations of said compartments.

2. A therapeutic cold pack for temporary affixation to an area of the human body, said cold pack comprising:
   (a) a pair of hermetic barrier layers that are heat sealed together throughout a plurality of intersecting articulations defining a plurality of compartments;
   (b) a refrigerant gel contained within said compartments, said refrigerant gel having a high specific heat such that after becoming cooled it absorbs a large quantity of heat while undergoing phase change on heating;
   (c) said plurality of compartments being of equal size and shape that are distributed radially about a central axis normal to said compartments;
   (d) adjoining ones of said compartments being hinged to each other along axes, certain of said axes being skewed with respect to others of said axes;
   (e) said compartments being adapted to be folded with respect to each other along said axes into a configuration that is snugly seated against an irregular three dimensional anatomical surface;
   (f) an extensive fastener area on the back of said cold pack;
   (g) at least a strap having at least a restricted fastener area;
   (h) said restricted fastener area of said strap being engageable with any part of said extensive fastener area on said cold pack to secure said compartments in said configuration;
   (i) said gel being fluid at its operating temperature;
   (j) said first fastener area and said second fastener area including mating surfaces;
   (k) said mating surfaces including micro-loop surfaces and micro-hook surfaces;

(l) said hermetic barrier layers being composed of polyurethane sheet;

(m) said refrigerant gel including an aqueous dispersion of ethylene glycol;

(n) said compartments being arranged in cloverleaf fashion about an axial hole located about said central axis, said articulations being wedge shaped.

3. A therapeutic cold pack for temporary affixation to an area of the human body, said cold pack comprising:

(a) a pair of hermetic barrier layers that are heat sealed together throughout a plurality of intersecting articulations defining a plurality of compartments;

(b) a refrigerant gel contained within said compartments, said refrigerant gel having a high specific heat such that after becoming cooled it absorbs a large quantity of heat while undergoing phase change on heating;

(c) said plurality of compartments being distributed throughout an extended area;

(d) adjoining ones of said compartments being hinged to each other along axes, certain of said axes being skewed with respect to others of said axes;

(e) said compartments being adapted to be folded with respect to each other along said axes into a configuration that is snugly seated against an irregular three dimensional anatomical surface;

(f) an extensive fastener area on the back of said cold pack;

(g) at least a strap having at least a restricted fastener area;

(h) said restricted fastener area of said strap being engageable with any part of said extensive fastener area on said cold pack to secure said compartments in said configuration;

(i) said gel being fluid at its operating temperature;

(j) said first fastener area and said second fastener area including mating surfaces;

(k) said mating surfaces include micro-loop surfaces and micro-hook surfaces;

(l) said hermetic barrier layers being composed of polyurethane sheet;

(m) said refrigerant gel including an aqueous dispersion of ethylene glycol;

(n) said compartments being arranged in a pair of oppositely directed multilaterally-shaped assemblages, separated by a pair of elastic straps, said assemblages including forward compartments for hugging the metatarsal, intermediate compartments for hugging the ankle, and upper compartments for hugging the lower leg;

(o) said multilaterally-shaped assemblages being substantially mirror images of each other.

* * * * *